US010071358B2

(12) United States Patent
Qiu

(10) Patent No.: US 10,071,358 B2
(45) Date of Patent: Sep. 11, 2018

(54) ANTIBIOTIC PREPARATION METHOD AND PLATFORM SYSTEM BASED ON SAME

(71) Applicant: PROTEIN DESIGN LAB, LTD., Beijing (CN)

(72) Inventor: Xiaoqing Qiu, Beijing (CN)

(73) Assignee: PROTEIN DESIGN LAB, LTD., Beijing (CN)

( * ) Notice: Subject to any disclaimer, the term of this patent is extended or adjusted under 35 U.S.C. 154(b) by 863 days.

(21) Appl. No.: 14/363,773

(22) PCT Filed: Dec. 10, 2012

(86) PCT No.: PCT/CN2012/086296
§ 371 (c)(1),
(2) Date: Jun. 6, 2014

(87) PCT Pub. No.: WO2013/083095
PCT Pub. Date: Jun. 13, 2013

(65) Prior Publication Data

US 2014/0349880 A1 Nov. 27, 2014

(30) Foreign Application Priority Data

Dec. 8, 2011 (CN) .......................... 2011 1 0405775

(51) Int. Cl.
*G01N 33/569* (2006.01)
*C40B 30/04* (2006.01)
(Continued)

(52) U.S. Cl.
CPC ......... *B01J 19/0046* (2013.01); *A61K 39/395* (2013.01); *C07K 14/21* (2013.01);
(Continued)

(58) Field of Classification Search
CPC ........................... B01J 19/0046; G01N 33/569
(Continued)

(56) References Cited

U.S. PATENT DOCUMENTS

2013/0142797 A1 6/2013 Qiu
2014/0170170 A1 6/2014 Qiu

FOREIGN PATENT DOCUMENTS

CN 1641024 7/2005
CN 101200727 6/2008
(Continued)

OTHER PUBLICATIONS

Qui et al., Small Antibody Mimetics Comprising Two Complimentarity-Determining Regions and a Framework Region for Tumor Targeting, Nature Biotechnology, 2007, 25(8), 921-929.*
(Continued)

*Primary Examiner* — Amy M Bunker
(74) *Attorney, Agent, or Firm* — Morrison & Foerster LLP

(57) ABSTRACT

Provided are a novel antibiotic preparation method and platform system based on the method, belonging to a novel drug development method. The method is based on a fixed structural formula: F—R, wherein F is an effect area, and R is an identification area. At the prior art level, the present invention can quickly develop a specific novel antibiotic for most pathogenic microorganisms or biological cells. Also provided is a platform for implementing the method, ensuring that the novel antibiotic is developed in an efficient streamlined process.

12 Claims, 4 Drawing Sheets

Specification includes a Sequence Listing.

(51) Int. Cl.

| | |
|---|---|
| ***B01J 19/00*** | (2006.01) |
| ***A61K 39/395*** | (2006.01) |
| ***C07K 16/00*** | (2006.01) |
| ***C07K 14/21*** | (2006.01) |
| ***C07K 14/245*** | (2006.01) |
| ***C07K 16/08*** | (2006.01) |
| ***C07K 16/12*** | (2006.01) |

(52) U.S. Cl.
CPC ............ *C07K 14/245* (2013.01); *C07K 16/00* (2013.01); *C07K 16/085* (2013.01); *C07K 16/1203* (2013.01); *G01N 33/569* (2013.01); *B01J 2219/00583* (2013.01); *B01J 2219/00725* (2013.01); *C07K 2317/73* (2013.01); *C07K 2319/00* (2013.01); *G01N 2500/04* (2013.01)

(58) Field of Classification Search
USPC .............................................................. 506/9
See application file for complete search history.

(56) References Cited

FOREIGN PATENT DOCUMENTS

| | | | | |
|---|---|---|---|---|
| CN | 101215568 | | 7/2008 | |
| CN | 101633699 | | 1/2010 | |
| CN | 101633699 A | * | 1/2010 | ....... A61K 47/48484 |
| CN | 101643501 | | 2/2010 | |
| CN | 102747041 | | 10/2012 | |
| EP | 2474558 | | 7/2012 | |
| EP | 2474558 A1 | * | 7/2012 | ....... A61K 47/48484 |
| EP | 2700710 A1 | | 2/2014 | |
| WO | WO-2006/103494 | | 10/2006 | |
| WO | WO-2011026447 | | 3/2011 | |
| WO | WO 2011026447 A1 | * | 3/2011 | ....... A61K 47/48484 |

OTHER PUBLICATIONS

Lindberg et al., Identification of Specific Residues in Colicin E1 Involved in Immunity Protein Recognition, Journal of Bacteriology, 2001, 183(6), 2132-2136.*

Chen et al., An Interesting Design of Fusion Protein to Kill Glioma Cell Line of U-87 MG Cells, Scientific Reserach and Essays, 2011, 6(24), 5153-5157.*

Qiu et al., An Engineered Multidomain Bactericidal Peptide as a Model for Targeted Antibiotics Against Specific Bacteria, Nature Biotechnology, 2003, 21(12), 1480-1485. (Year: 2003).*

International Preliminary Report on Patentability for PCT/CN2012/086296, dated Mar. 17, 2014, 15 pages (English translation included).

International Search Report for PCT/CN2012/086296, dated Mar. 14, 2013, 11 pages (English translation included).

Qiu et al., "Major transmembrane movement associated with colicin la channel gating," J Gen Physiol (1996) 107(3):313-328.

Qiu et al., "Small antibody mimetics comprising two complementarity-determining regions and a framework region for tumor targeting," Nat Biotechnol (2007) 25(8):921-929.

Written Opinion for PCT/CN2012/086296, dated Mar. 14, 2013, 4 pages.

* cited by examiner

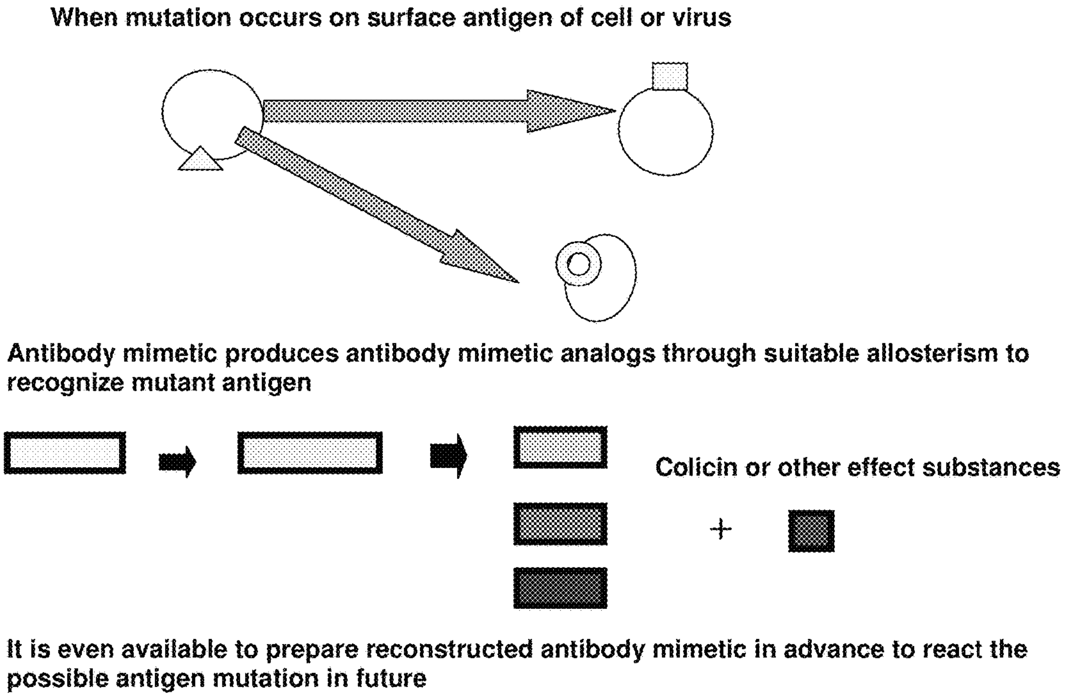
Figure 4
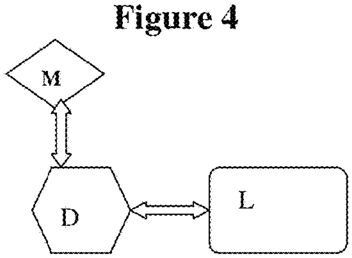
Figure 5
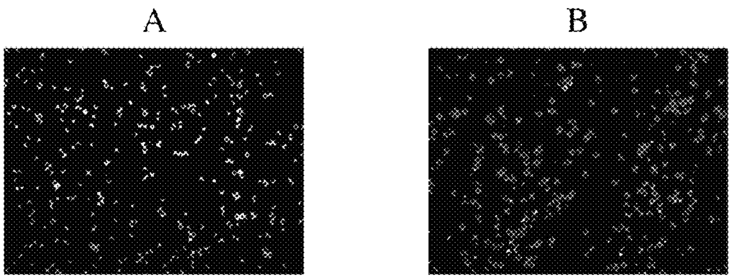
Figures 6 (A-B)

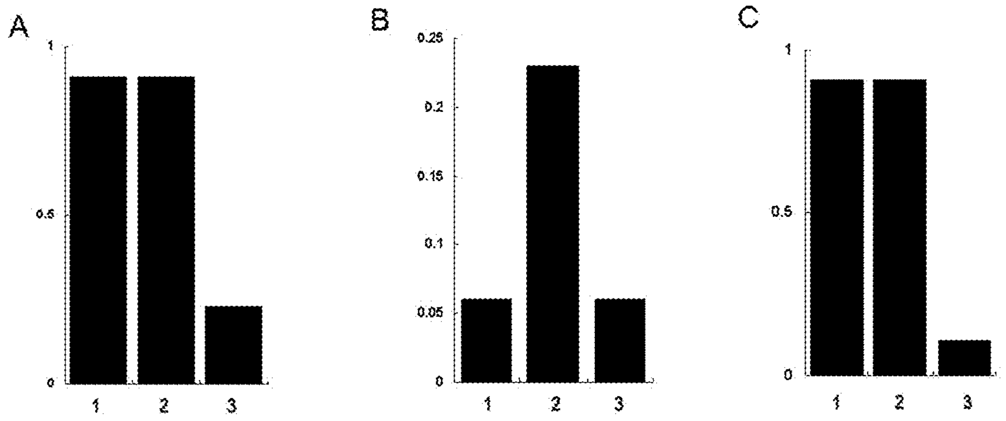
Figures 7 (A-C)
A
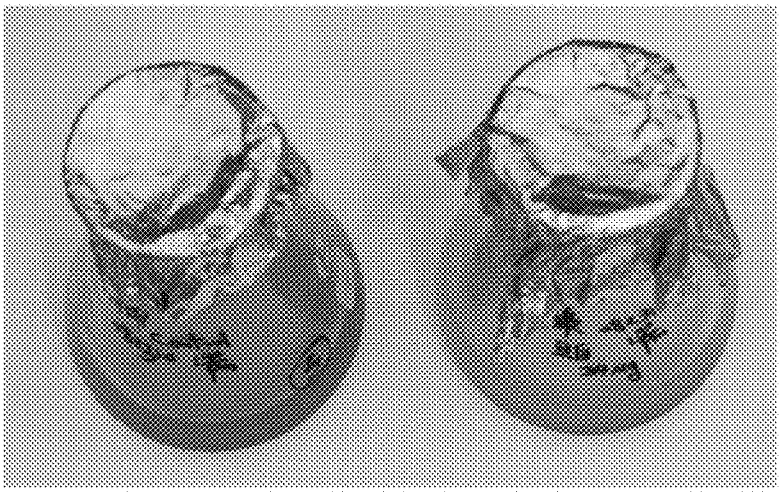
B
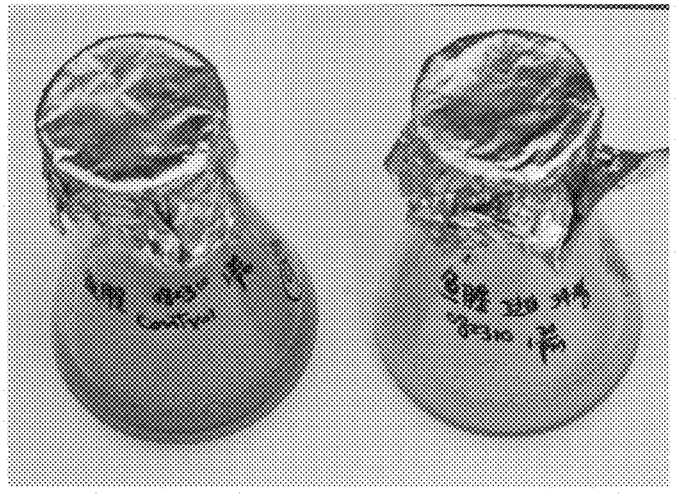
Figures 8 (A-B)

C
D
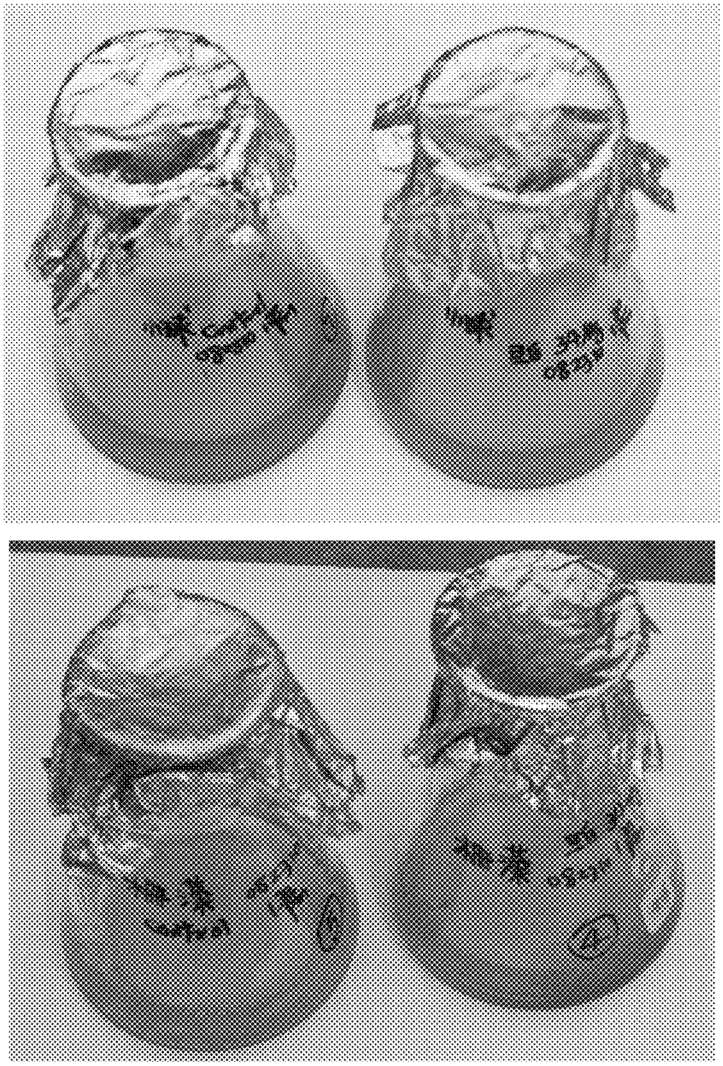
Figure 8 (C-D)

SEQUENCE LISTING

```
<160> NUMBER OF SEQ ID NOS: 33

<210> SEQ ID NO 1
<211> LENGTH: 625
<212> TYPE: PRT
<213> ORGANISM: Artificial Sequence
<220> FEATURE:
<223> OTHER INFORMATION: Mutant of colicin mutamer Ia

<400> SEQUENCE: 1

Ser Asp Pro Val Arg Ile Thr Asn Pro Ala Ala Glu Ser Leu Gly Tyr
1               5                   10                  15

Asp Ser Asp Gly Gly Glu Ile Met Gly Val Asp Ile Tyr Leu Asn Pro
            20                  25                  30

Pro Arg Val Asp Val Phe Asp Gly Thr Pro Pro Ala Trp Ser Ser Phe
```

-continued

```
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
    290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
        355                 360                 365

Val Ala Glu Trp Asp Lys Leu Arg Gln Arg Leu Leu Asp Ala Arg Asn
    370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
            420                 425                 430

Gln Lys Ile Ala Glu Glu Lys Arg Lys Gln Asp Glu Leu Lys Ala Thr
        435                 440                 445

Lys Asp Ala Ile Asn Phe Thr Thr Glu Phe Leu Lys Ser Val Ser Glu
    450                 455                 460
```

-continued

```
Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510

Ala Ala Ile Ala Ala Ala Leu Glu Ser Val Lys Leu Ser Asp Ile Ser
        515                 520                 525

Ser Asn Leu Asn Arg Phe Ser Arg Gly Leu Gly Tyr Ala Gly Lys Phe
    530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
    610                 615                 620

Ile
625


<210> SEQ ID NO 2
<211> LENGTH: 28
<212> TYPE: PRT
<213> ORGANISM: Artificial Sequence
<220> FEATURE:
<223> OTHER INFORMATION: VHCDR1-VHFR2-VLCDR3

<400> SEQUENCE: 2

Ser Phe Gly Met His Trp Val Arg Gln Ala Pro Glu Lys Gly Leu Glu
1               5                   10                  15

Trp Val Ala Gly Gln Gly Tyr Ser Tyr Pro Tyr Thr
            20                  25


<210> SEQ ID NO 3
<211> LENGTH: 28
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 3

Ser Tyr Gly Met His Trp Val Arg Gln Ala Pro Glu Lys Gly Leu Glu
1               5                   10                  15

Trp Val Ala Gly Gln Gly Tyr Ser Tyr Pro Tyr Thr
            20                  25


<210> SEQ ID NO 4
<211> LENGTH: 28
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 4

Ser Phe Gly Met His Trp Val Arg Gln Ala Pro Glu Lys Gly Leu Glu
1               5                   10                  15
```

-continued

```
Trp Val Ala Gln Gln Trp Ser Ser Asn Pro Tyr Thr
            20                  25


<210> SEQ ID NO 5
<211> LENGTH: 28
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 5

Ser Phe Gly Met His Trp Val Arg Gln Ala Pro Glu Lys Gly Leu Glu
1               5                   10                  15

Trp Val Ala Leu Gln Gly Thr His Gln Pro Tyr Thr
            20                  25


<210> SEQ ID NO 6
<211> LENGTH: 28
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 6

Ser Phe Gly Met His Trp Val Arg Gln Ala Pro Glu Lys Gly Leu Glu
1               5                   10                  15

Trp Val Ala Gln Gln Leu His Phe Tyr Pro His Thr
            20                  25


<210> SEQ ID NO 7
<211> LENGTH: 28
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 7

Arg Gln Gly Met His Trp Val Arg Gln Ala Pro Glu Lys Gly Leu Glu
1               5                   10                  15

Trp Val Ala Gly Gln Gly Tyr Ser Tyr Pro Tyr Thr
            20                  25


<210> SEQ ID NO 8
<211> LENGTH: 27
<212> TYPE: PRT
<213> ORGANISM: Artificial Sequence
<220> FEATURE:
<223> OTHER INFORMATION: VHCDR1-VHFR2-VLCDR3

<400> SEQUENCE: 8

Ser Tyr Trp Leu His Trp Ile Lys Gln Arg Pro Gly Gln Gly Leu Trp
1               5                   10                  15

Ile Gly Ser Gln Ser Thr His Val Pro Arg Thr
            20                  25


<210> SEQ ID NO 9
<211> LENGTH: 27
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 9

Ser Tyr Gly Met His Trp Ile Lys Gln Arg Pro Gly Gln Gly Leu Trp
1               5                   10                  15
```

-continued

```
Ile Gly Ser Gln Ser Thr His Val Pro Arg Thr
            20                  25


<210> SEQ ID NO 10
<211> LENGTH: 27
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 10

Ser Tyr Trp Ile Glu Trp Ile Lys Gln Arg Pro Gly Gln Gly Leu Trp
1               5                   10                  15

Ile Gly Ser Gln Ser Thr His Val Pro Arg Thr
            20                  25


<210> SEQ ID NO 11
<211> LENGTH: 27
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 11

Asn Tyr Trp Met His Trp Ile Lys Gln Arg Pro Gly Gln Gly Leu Trp
1               5                   10                  15

Ile Gly Ser Gln Ser Thr His Val Pro Arg Thr
            20                  25


<210> SEQ ID NO 12
<211> LENGTH: 27
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 12

Ser Tyr Trp Leu His Trp Ile Lys Gln Arg Pro Gly Gln Gly Leu Trp
1               5                   10                  15

Ile Gly Met Gln Asn Ile Gly Leu Pro Trp Thr
            20                  25


<210> SEQ ID NO 13
<211> LENGTH: 27
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 13

Ser Tyr Trp Leu His Trp Ile Lys Gln Arg Pro Gly Gln Gly Leu Trp
1               5                   10                  15

Ile Gly Gln Gln Phe Thr Ser Ser Pro Tyr Thr
            20                  25


<210> SEQ ID NO 14
<211> LENGTH: 26
<212> TYPE: PRT
<213> ORGANISM: Artificial Sequence
<220> FEATURE:
<223> OTHER INFORMATION: VHCDR1-VHFR2-VLCDR3

<400> SEQUENCE: 14

Ser Thr Ala Leu His Trp Arg Gln Ala Pro Gly Lys Gly Leu Glu Trp
```

-continued

```
1               5                   10                  15

Val Pro Arg Tyr Asp Glu Phe Pro Tyr Thr
            20                  25


<210> SEQ ID NO 15
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 15

Ser Phe Gly Met His Trp Arg Gln Ala Pro Gly Lys Gly Leu Glu Trp
1               5                   10                  15

Val Pro Arg Tyr Asp Glu Phe Pro Tyr Thr
            20                  25


<210> SEQ ID NO 16
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 16

Asn Tyr Trp Met His Trp Arg Gln Ala Pro Gly Lys Gly Leu Glu Trp
1               5                   10                  15

Val Pro Arg Tyr Asp Glu Phe Pro Tyr Thr
            20                  25


<210> SEQ ID NO 17
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 17

Ser Thr Ala Leu His Trp Arg Gln Ala Pro Gly Lys Gly Leu Glu Trp
1               5                   10                  15

Val Phe Gln Gly Ser His Val Pro Phe Thr
            20                  25


<210> SEQ ID NO 18
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 18

Ser Thr Ala Leu His Trp Arg Gln Ala Pro Gly Lys Gly Leu Glu Trp
1               5                   10                  15

Val Tyr Cys His Gln Trp Ser Met Tyr Thr
            20                  25


<210> SEQ ID NO 19
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 19
```

-continued

Ser Thr Ala Leu His Trp Arg Gln Ala Pro Gly Lys Gly Leu Glu Trp
1 5 10 15

Val Gln Gln Trp Ser Ser Asn Pro Tyr Thr
20 25

<210> SEQ ID NO 20
<211> LENGTH: 26
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 20

Ser Thr Ala Leu His Trp Arg Gln Ala Pro Gly Lys Gly Leu Glu Trp
1 5 10 15

Val Gln Gln Phe Thr Ser Ser Pro Tyr Thr
20 25

<210> SEQ ID NO 21
<211> LENGTH: 14
<212> TYPE: PRT
<213> ORGANISM: Candida albicans

<400> SEQUENCE: 21

Gly Phe Arg Leu Tyr Asn Phe Gly Tyr Phe Glu Pro Gly Lys
1 5 10

<210> SEQ ID NO 22
<211> LENGTH: 8
<212> TYPE: PRT
<213> ORGANISM: Staphyloccocus aureus

<400> SEQUENCE: 22

Tyr Ser Thr Cys Asp Phe Ile Met
1 5

<210> SEQ ID NO 23
<211> LENGTH: 9
<212> TYPE: PRT
<213> ORGANISM: Staphyloccocus aureus

<400> SEQUENCE: 23

Gly Val Asn Ala Cys Ser Ser Leu Phe
1 5

<210> SEQ ID NO 24
<211> LENGTH: 8
<212> TYPE: PRT
<213> ORGANISM: Staphyloccocus aureus

<400> SEQUENCE: 24

Tyr Ile Asn Cys Asp Phe Leu Leu
1 5

<210> SEQ ID NO 25
<211> LENGTH: 8
<212> TYPE: PRT
<213> ORGANISM: Staphyloccocus aureus

<400> SEQUENCE: 25

Tyr Ser Thr Cys Tyr Phe Ile Met
1 5

<210> SEQ ID NO 26

```
<211> LENGTH: 8
<212> TYPE: PRT
<213> ORGANISM: Staphylococcus epidermidis

<400> SEQUENCE: 26

Asp Ser Val Cys Ala Ser Tyr Phe
1               5


<210> SEQ ID NO 27
<211> LENGTH: 29
<212> TYPE: PRT
<213> ORGANISM: Artificial Sequence
<220> FEATURE:
<223> OTHER INFORMATION: VHCDR1-VHFR2-VLCDR3

<400> SEQUENCE: 27

Ser Tyr Trp Met Gln Trp Val Lys Gln Arg Pro Gly Gln Gly Leu Glu
1               5                   10                  15

Trp Ile Gly Gln Gln Tyr Trp Ser Thr Pro Pro Trp Thr
            20                  25


<210> SEQ ID NO 28
<211> LENGTH: 29
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 28

Ser Tyr Gly Met His Trp Val Lys Gln Arg Pro Gly Gln Gly Leu Glu
1               5                   10                  15

Trp Ile Gly Gln Gln Tyr Trp Ser Thr Pro Pro Trp Thr
            20                  25


<210> SEQ ID NO 29
<211> LENGTH: 29
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 29

Asp His Tyr Met His Trp Val Lys Gln Arg Pro Gly Gln Gly Leu Glu
1               5                   10                  15

Trp Ile Gly Gln Gln Tyr Trp Ser Thr Pro Pro Trp Thr
            20                  25


<210> SEQ ID NO 30
<211> LENGTH: 29
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 30

Ser Tyr Trp Ile Glu Trp Val Lys Gln Arg Pro Gly Gln Gly Leu Glu
1               5                   10                  15

Trp Ile Gly Gln Gln Tyr Trp Ser Thr Pro Pro Trp Thr
            20                  25


<210> SEQ ID NO 31
<211> LENGTH: 29
<212> TYPE: PRT
<213> ORGANISM: Artificial Sequence
<220> FEATURE:
```

-continued

```
<223> OTHER INFORMATION: Point-mutant of VHCDR1-VHFR2-VLCDR3

<400> SEQUENCE: 31

Ser Tyr Trp Met Gln Trp Val Lys Gln Arg Pro Gly Gln Gly Leu Glu
1               5                   10                  15

Trp Ile Gly Gln Gln Gln Phe Thr Ser Ser Pro Trp Thr
            20                  25


<210> SEQ ID NO 32
<211> LENGTH: 29
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 32

Ser Tyr Trp Met Gln Trp Val Lys Gln Arg Pro Gly Gln Gly Leu Glu
1               5                   10                  15

Trp Ile Gly Gln Gln Gln Ser Arg Glu Tyr Pro Tyr Thr
            20                  25


<210> SEQ ID NO 33
<211> LENGTH: 29
<212> TYPE: PRT
<213> ORGANISM: Artificial Sequence
<220> FEATURE:
<223> OTHER INFORMATION: Point-mutant of VHCDR1-VHFR2-VLCDR3

<400> SEQUENCE: 33

Ser Tyr Trp Met Gln Trp Val Lys Gln Arg Pro Gly Gln Gly Leu Glu
1               5                   10                  15

Trp Ile Gly Gln Leu Gln Gly Thr His Gln Pro Tyr Thr
            20                  25
```

ANTIBIOTIC PREPARATION METHOD AND PLATFORM SYSTEM BASED ON SAME

CROSS-REFERENCE TO RELATED APPLICATION

This application is the national phase of PCT application PCT/CN2012/086296 having an international filing date of Dec. 10, 2012, which claims priority from Chinese patent application 201110405775.3, filed Dec. 8, 2011. The contents of these prior applications are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717412000600SeqList.txt, date recorded: Jun. 6, 2014, size: 16,207 bytes)

TECHNICAL FIELD

This invention relates to biological medicine developing technology, especially to a novel antibiotic preparation method and platform system based on same.

BACKGROUND ART

Currently, the research and development of pharmaceutical industry, particularly antibiotic, is facing difficulties: 1. There are more and more drug-resistant pathogenic bacteria. Current antibiotics do not pose a threat to drug-resistant pathogenic bacteria. Mortality rate caused by these drug-resistant pathogenic bacteria is increasing. 2. The speed of novel medicine developing is far behind the occurring pace of drug-resistant pathogenic bacteria. It needs long time and costs much to screen antibiotics with traditional methods as well as obtain the achievement from the research and development. 3. The novel antibiotics developed by gene engineering or biotechnology are still easy to result in drug-resistance of pathogenic bacteria.

It was shown by statistics data of World Health Organization (WHO) that, in millions of people infected with drug-resistant *Staphylococcus aureus* every year, around 30% of said people die finally—which is higher than the mortality rate of AIDS. In order to cure infection of drug-resistant *Staphylococcus aureus*, the cost of whole world exceeds 20 billion USD every year. After drug-resistant *Staphylococcus aureus* occurred, vancomycin became the main role to cure *Staphylococcus aureus* infection. However, there has been vancomycin-resistant *Staphylococcus aureus* occurred in hospital since 2002. Although the spreading area of vancomycin-resistant *Staphylococcus aureus* is small at present, there is little medicine that can inhibit them effectively, so the mortality rate caused by infection of vancomycin-resistant *Staphylococcus aureus* is very high. In the latest 10 years, another drug-resistant bacteria—multi-drug-resistant Gram-negative bacteria occurred, and they have stronger drug-resistance. Almost none of antibiotics used in current clinical medicine can threaten said drug-resistant bacteria.

Currently most of antibiotics are produced by bacteria and fungi, or derived from natural antibiotics by chemical modification. The traditional screening method for antibiotics comprises isolating microorganisms from soil samples, extracting secretions from medium for growing said microorganisms, detecting substance with antibacterial or sterilizing effects in said secretions and separating individual medicine ingredients with potential medicinal value. The method was very effective in golden age of developing antibiotics (1940-1950). But it comes to the end now, as said screening method depends on secretions of bacteria and fungi in nature, namely the novel antibiotics are obtained by screening and modifying secretions of discovered microorganisms. Said traditional method for developing antibiotics requires long time unavoidably, and has uncertain outcome. Thus, in the past 50 years, pharmaceutical companies never stopped screening antibiotics, but novel antibiotics screened are less and less. It is demonstrated by statistics data of Infectious Diseases Society of America (IDSA) that, in recent new medicine applications of FDA in US, there are only 16 novel antibiotics applications, and there is no one patent application about antibiotic against highly-drug-resistant Gram-negative bacteria. The famous popular science magazine "*Scientific American*" had warned continuously from 2009 to 2012 that, super bacteria are threatening human life safety. CDC in US forecast that the current used antibiotics would become invalid totally 10-20 years later. The New York Times reports that, due to abusing antibiotics in agriculture, human would go back to the times without any available antibiotics 5 years later, and NDM-1 super bacterium mutant genes has led to panic in the world. The problem of antibiotics and drug-resistant bacteria in stock-breeding is also a serious problem, and has influenced agricultural product safety. The recent 40 years is a vacuum period of antibiotics development. In a word, the speed of developing and researching novel medicine is far behind the pace of drug-resistant bacteria mutation.

At present, there are two methods for developing novel antibiotics: (1) modifying current antibiotics or synthesizing new type of antibiotics, (2) conducting gene modification on bacteria synthesizing antibiotics. However, both of said two methods have not overstepped such a keynote that: antibacterial mechanism of said antibiotics is not novel to bacteria. Therefore, without exception, the bacteria will generate drug-resistance to said "novel" antibiotics soon.

In order to resist pathogenic microorganisms with strong variability, strong viability, strong pathogenicity and various species, the problems urgent to be solved currently are as follows:

1. providing antibiotics with stronger antibacterial or sterilizing effects to pathogenic bacteria, especially to drug-resistant pathogenic bacteria;
2. providing methods for preparing said antibiotics in clause 1, preferably methods which can response to variability of pathogenic bacteria, i.e., developing and researching methods of antibiotics with short development cycle, which can sensitively resist new or variant pathogenic microorganisms;
3. said antibiotics developed by said method will not lead to drug-resistance of pathogenic microorganisms in a short time.

However, the above-mentioned problems are just "conundrums" which have not been solved by current several generations of antibiotics and traditional antibiotics developing methods.

DISCLOSURE OF THE INVENTION

In view of technical difficulties of obtaining novel antibiotics existing in above-mentioned fields, provided is a method and platform different from traditional strategies for developing antibiotics. Through said method and platform, novel antibiotics with specific recognition and killing capacity against any pathogenic microorganism, target cell or target tissue can be offered in a short term; said methods can sensitively solve drug-resistance raised due to continuous mutation of pathogenic microorganism, i.e., promptly provides corresponding novel antibiotics against newly-raised variant strains. And said novel antibiotics prepared by said method rarely lead to variance of pathogenic microorganism as well as drug-resistance, due to their novel sterilization mechanism. Technical solution of this invention is as follows:

A novel antibiotic preparation method, wherein steps are as follows:

(1) determining targets: said targets refer to prokaryotic cells, eukaryotic cells, viruses or products thereof which said novel antibiotic will react against directly;

(2) designing molecular structure of said novel antibiotic:

said molecular structure of said novel antibiotic is designed according to the following general formula:

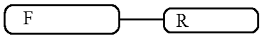

wherein, R is recognition region, which specifically recognizes or combines said targets; F is effect region, which generates pharmaceutical effects to targets, and said pharmaceutical effects are effects of regulating, repairing, labeling, causing death and/or collapsing against said targets specifically;

establishing recognition region molecular structure library;

establishing effect region molecular structure library;

according to said general formula, designing recombinant molecular structure library on the basis of said recognition region molecular structure library and effect region molecular structure library;

said designing refers to the process of structural readjustment, structural recombination and/or structural confirmation carried out on the basis of molecular structures of collected, selected or prepared substances used as effect region or recognition region;

(3) based on said recombinant molecular structure library, preparing and verifying recombinant so as to obtain candidate novel antibiotics;

(4) screening novel antibiotics which meet medicine requirement from candidate novel antibiotics.

Said establishing recognition region molecular structure library refers to collecting currently-known natural substances which specifically recognize and/or combine said targets by searching and analyzing; or/and artificially preparing artificial substances which specifically recognize and/or combine said targets.

Said natural substances refer to natural bioactive molecular, or recognition region of bacteriophage, which can be recognized by acceptor of said targets; said artificial substances refer to antibody mimetic, said antibody mimetic is designed according to amino acid sequence of immunoglobulin which can specifically recognize unique substance on said targets.

Said antibody mimetic is short peptide with a structure of $V_H$CDR1-$V_H$FR2-$V_L$CDR3 from N-terminal to C-terminal, which is constituted by the regions of $V_H$CDR1, $V_H$FR2, $V_L$CDR3 on Fab short arm of said immunoglobulin; or is mutamer of said short peptide; said mutamer refers to product obtained by artificial site-mutation to 5 amino acid residues of $V_H$CDR1 and 9 amino acid residues of $V_L$CDR3 on short peptide, which preserves recognition capability to unique substance on said targets.

Said immunoglobulin can be multiple, e.g., $V_H$CDR1 of $V_H$CDR1-$V_H$FR2-$V_L$CDR3 is from one immunoglobulin, and $V_L$CDR3 is from another immunoglobulin.

Said immunoglobulin is prepared by taking unique substance on target as immunogen to immunize animal.

Said immunoglobulin is prepared by taking common unique substances on multiple targets as immunogens to immunize animal.

Said immunoglobulin is prepared by taking multiple unique substances on target as immunogens respectively to immunize animal.

When said target refers to virus, prokaryotic cell or eukaryotic cell with phospholipid bilayer membranes as the basic structure of its cell membrane or envelope, said pharmaceutical effect refers to causing death and/or collapsing; said effect region refers to bioactive substance which can form ion channel or pore path on phospholipid bilayer membranes.

Said effect region refers to *Pseudomonas aeruginosa* bacteriocin pyocin.

Said effect region refers to colicins E1, Ia, Ib, A, B or N; or domains of colicin molecules E1, Ia, Ib, A, B and/or N which can form ion channels; or molecules obtained by allosterism from colicin molecules E1, Ia, Ib, A, B or N, or from domains of colicin molecules E1, Ia, Ib, A, B or N which can form ion channels, having function of forming ion channels in said phospholipid bilayer membranes.

Said recombinant is recombinant polypeptide, said preparing recombinant refers to that gene coding said recombinant polypeptide is transformed into biological expression system to express fusion protein, and candidate novel antibiotic is obtained by separating and purifying fusion protein.

Said biological expression system refers to *Escherichia coli* pET system engineering bacteria *E. coli* B834 (DE3).

Said pharmaceutical effect refers to labeling, said effect region refers to label, said preparing recombinant refers to linking effect region and recognition region operably.

Novel antibiotic preparation platform system comprises 3 interoperable systems: (1) goal proposing system, (2) designing system, (3) laboratory system;

said platform prepares novel antibiotic according to said method of any one of the claims; said goal proposing system determines development goal, and delivers task instruction to said designing system;

said designing system establishes recognition region molecular structure library as well as effect region molecular structure library, designs molecular structure library for said recombinant, and provides said molecular structure library to said laboratory system, said laboratory system offers experimental results to said designing system; said designing system reports the finally-selected candidate products as development results to marketing system;

said designing refers to the procedure of structural adjustment, structural recombination and/or structural confirmation based on molecular structure of the collected, selected or prepared substance used as effect region or recognition region.

Said laboratory system comprises at least one 3$^{rd}$ party partner institution which undertakes said experiments.

By the method for preparing novel antibiotics of this invention, it is available to prepare a batch of candidate novel antibiotics against most targets, and select novel antibiotics specifically against said targets with recognition region and effect region from candidates. In the method of this invention, said targets may be prokaryotic cells (e.g., *Staphylococcus aureus* with drug-resistance in Example 5, environmental pollutant-cyanobacteria in Example 6, *bacillus anthracis* in Example 3), eukaryotic cells (e.g., agricultural fungus against by antifungal polypeptide in Example 4, EB virus-induced tumor cells in Example 1), virus (e.g., unique envelope glycoprotein in EB virus in Example 1), products of said prokaryotic or eukaryotic cells.

During preparation, in accordance with general formula

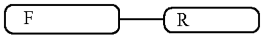

, establishing recognition region molecular structure library as well as effect region molecular structure library, and designing molecular structure library for recombinants.

Because there exist substances with specific recognition for specific species of cells in nature, such as, pheromone, ligand of acceptor on recognition cells, immunoglobulin produced in human or animal. Moreover, immunoglobulin against xenobiotic is produced naturally by immune system of animals. On the basis of immunoglobulin prepared through artificially immunizing animals or existing naturally, it is basically available to obtain recognition substances against any said target, which makes said method of this invention has a wide applicability.

Additionally, there also exist substances in nature, which can form lethal change on specific cells. For example, both of colicin and *Pseudomonas aeruginosa* bacteriocins can be conducted as effect region, but their disadvantage is that the species of target cells they react against are limited.

Taking advantages of above-mentioned two kinds of substances and adopting their strong points while overcoming own deficiencies, as to novel antibiotics prepared by the method of this invention, recognition region leads whole recombinant molecular to recognize target substances, and effect region completes pharmaceutical effects.

The principle of the method of this invention is preparing novel antibiotics based on a general formula, collecting and/or designing a batch of molecular structures of recognition region and effect region against target substance proposed to establish molecular structure library, then designing molecular structure of novel antibiotics according to established molecular structure library, and obtaining a batch of molecular structure libraries of recombinants; afterwards, preparing a batch of candidate novel antibiotics in line with molecular structural information of molecular structure libraries of recombinants, finally verifying said candidate novel antibiotics one by one to select novel antibiotic which meets pharmaceutical standards. The advantages of the preparation method of this invention are as follows:

(1) The method of this invention only aims against prokaryotic cells, eukaryotic cells, virus or products thereof to prepare novel antibiotics, and these above-mentioned substances either have natural recognition substances or have unique surface substances or their own can be conducted as immunogen for immunizing animal to obtain immunoglobulin which recognize themselves, which ensures that, it is available to always obtain recognition region by preparation method of this invention, and effectively breaks a bottleneck existing in current antibiotic development, i.e., the reality that proteins as targets of drug effect (i.e., drug targets) have been exhausted gradually, and the left targets are undruggable (i.e., do not react with drugs).

Moreover, there also exist substances as effect region in nature, but said substances have selectivity in connection with different pharmaceutical effects. For example, if the goal is to prepare a novel antibiotic to cause death of target cells, substances such as colicins are competent to achieve said goal; if the goal is to regulate, interfere or label, it is sufficient to select substance molecules with such effects as effect region. On the basis of general formula the method of this invention premised on, it is ensured that novel antibiotics can be prepared against most target substances, i.e., the method of this invention has high success rate and wide applicability.

(2) The best advantage of the method of this invention is that, against one target substance, several novel antibiotics can be prepared once time and they are well prepared to counter drug-resistance of pathogenic microorganism, because in this invention, novel antibiotics are prepared against some target substance based on a general formula; recombinants library is obtained by establishing effect region library and recognition region library respectively, and available recombinants with well effects are selected as novel antibiotics from recombinants library. This solves a problem existing in current new drug development that, the speed to occur drug-resistance in pathogenic microorganism is high, and there is no other alternative antibiotic when drug-resistance occurs.

In the method of this invention, when establishing recognition region library, specific monoclonal antibodies are preferably selected as the designed recognition region, i.e., they are designed as the commonly-designed single-chain antibodies, small molecular antibodies in prior art or antibody mimetic with structure shown in Table 1 which was disclosed by inventor of this invention previously. That is, molecular structure of the established recognition region may be antibody mimetic in Table 1 or point mutation products of said antibody mimetic; point mutation refers to short peptides obtained by conducting artificial point mutation on amino acid residue of two recognition regions composing antibody mimetic, which have recognition capacity against said target.

This makes members of the established recognition region molecular structure library expanded unlimitedly, so as to counter mutation of pathogen better, which amplifies the above second advantage of the method of this invention. For example, if target (pathogenic cell) is not recognized due to drug-resistance occurring on one recognition region, there can be many similar recognition region molecular structures as candidates.

Antibody mimetic has more advantages compared with antibody, and is easier to be obtained as well as operated artificially. Owing to different directed targets, substances conducted as recognition regions may be pheromone, phage recognition region or specific monoclonal antibodies which are collected from current database, but they are limited after all. In bioactive substances found in plants, animals or microorganisms, the most effective bioactive substance to recognize single molecule is antibody. In order to avoid the disadvantage of nature antibody with huge size, people always design and prepare antibody mutamer with smaller size. However, these mutamers consist of hundreds of amino acid residues, and still have huge size compared with recognition regions we seek. Fab short arm of each natural antibody has 6 antigen binding regions, and they as well as their backbone form complicated spatial structure. Said spatial structure has function of recognizing and binding specific antigen, while in novel antibiotics developed by the platform of this invention, it is sufficient that recognition region only has recognition function, and recognition region does not need to bind the corresponding antigen. According to Qiu, et al. ("Small antibody mimetic comprising two complementarity-determining regions and a framework region for tumor targeting," *Nature Biotechnology* 25(8): 921-929 (2007)), Qiu, et al., selected 2 antigen binding regions and one backbone region on Fab short arm of natural antibody to form a short peptide antibody mimetic referring to structure of natural antibody; although its size was 50-300 times smaller than natural antibody, it preserves basic biological activity of natural antibody, i.e., it can recognize some antigen specifically. Because immune system in human or animals will respond to produce immunoglobulin specifically against said immunogen when irritated by immunogen, this invention preferably prepares monoclonal antibodies recognizing targets and provides recognition region based on the monoclonal antibodies and the antibody mimetic designing idea disclosed in article of Qiu, et al., 2007. Thus, aiming at any pathogenic microorganism cell or pending-treated cell, specific monoclonal antibodies can be prepared theoretically, and suitable recognition region substances—antibody mimetic can be prepared correspondingly. This makes that the success rate to prepare novel antibiotics against some targets by the method of this invention has qualitative leap comparing with traditional method for preparing antibiotics, and the time to obtain products is shortened a lot. Theoretically, the time to prepare a novel antibiotic even a batch of novel antibiotics against one target equals to the time to obtain specific monoclonal antibody and the time to prepare recombinant protein by bio-engineering method.

Said targets are multiple targets with common surface antigen, and said antibody mimetic is prepared by immunizing animal with said common surface antigen as antigen composition. Novel antibiotics prepared by taking said antibody mimetic as recognition region can recognize several said targets, i.e., they have effects of broad-spectrum antibiotics.

With regard to recognition region molecular structure library established by the method of this invention, if specific substance on the selected target surface is common for various microorganism surfaces, the corresponding antibody mimetic becomes a broad-spectrum recognition region, that is, only if its surface has similar substances, the microorganism cell can be recognized, and the prepared novel antibiotic against it is broad-spectrum antibiotic. If the selected specific substance is unique for one microorganism cell, the corresponding antibody mimetic becomes a narrow-spectrum recognition region, and only the microorganism cell with similar substance can be recognized.

Taking various surface substances on the selected targets as immunogens, generating corresponding monoclonal antibodies by taking said surface substances separately to immunize animal to obtain many kinds of antibody mimetic and mutamer thereof which can recognize said microorganism cell specifically, is another approach to expand recognition region library. It is available to firstly select any one of these antibody mimetic as the first recognition region of novel antibiotic developed by the method of this invention. After being used practically for a period of time, if said microorganism has occurred drug-resistance against said recognition region (e.g., structure of the corresponding surface substance (antigen) is modified to keep said recognition region from being recognized), it is available to select another from these antibody mimetic as the second recognition region, the third recognition region, the fourth recognition region of novel antibiotic developed by the method of this invention, accordingly to offer various optional novel antibiotics, which effectively overcomes the difficulty of failing to immediately provide alternative drug for treatment after drug-resistance occurring against antibiotics in prior art. The method of this invention is capable to extend the effective application lifetime of one novel antibiotic.

When said target refers to virus, prokaryotic cell or eukaryotic cell with phospholipid bilayer membranes as the basic structure of its cell membrane or envelope, said pharmaceutical effect refers to causing death and/or collapsing, said effect region refers to bioactive substance which can form ion channel or pore path on phospholipid bilayer membranes, such as the currently known colicin and *Pseudomonas aeruginosa* bacteriocin pyocin.

Said effect region refers to colicins E1, Ia, Ib, A, B or N; or refers to domains of colicin molecules E1, Ia, Ib, A, B and/or N which can form ion channels;

or refers to molecules obtained by allosterism from colicin molecules E1, Ia, Ib, A, B or N, or from domains of colicin molecules E1, Ia, Ib, A, B or N which can form ion channels, having function of forming ion channels in said phospholipid bilayer membranes. It is illustrated according to description of background art that, main pathogenic microorganisms confronted by human currently and in future have a common characteristic that their cell membranes have a structure of phospholipid bilayer membranes. In nature, there exist many bacteriocins which kill bacteria by directly forming ion channel through cell membranes of bacteria. The typical representation is a bacteriocin secreted by *Escherichia coli*-colicin, and its function is to kill *Escherichia coli* of the same species but different strains, rather than hurt other species of bacteria and host of *Escherichia coli*-human as well as animals. As a model sample of colicins which forms ion channel, after colicin Ia was found by Jacob in 1952, transmembrane spatial structure of ion channel formed by colicin Ia in artificial lipid bilayer membranes in the state of opening or closing was finally demonstrated in 1996 (Qiu, et al., "Major transmembrane movement associated with colicin Ia channel gating," *J. Gen. Physiology,* 107:313-328 (1996)), which laid a theoretical basis for designing and preparing novel antibiotics on molecular level. However, wild-type colicin only reacts on *Escherichia coli* of the same species but different strains, and it is necessary to alter its targeting to make colicin attack other pathogenic bacteria. Therefore, colicin is an ideal candidate of effect region of novel antibiotic developed by the platform of this invention.

When said recombinant is recombinant polypeptide, above-mentioned linking effect region and recognition region refers to that gene coding said recombinant polypeptide is transformed into biological expression system to express fusion protein, and novel antibiotic is obtained by separating and purifying fusion protein.

Said pharmaceutical effect refers to labeling, said effect region refers to label, said preparing recombinant refers to linking effect region and recognition region operatively. For example, the molecule of recognition region can be labelled with radioactive marker.

Concerning the method of this invention, after recognition region molecule is confirmed against target, effect region molecule is selected, and selection of effect region molecule is relative to the goal of establishing said antibiotic. For example, if the goal is to regulate against target, it is available to select molecule with repairing function; if the goal is to cause target dead or limit its growth and development, it is available to select biological polypeptide molecule which can form lethal ion channel through target's cell membrane, like colicin; if the goal is to label or image target, it is available to link label or imaging agent to recognition region to obtain novel antibiotic for labeling, and label is bound to target through recognition region, in order to conduct continuous therapy or research against labeling cells.

In the method of this invention for developing novel antibiotics, the important work is to establish recognition region library, because most targets have phospholipid bilayer as the basic structure of their cell membrane or envelop. In the method of this invention, colicin, *Pseudomonas aeruginosa* bacteriocin pyocin are preferably selected as effect region. Colicin is an effective regulation motivation for survival competition and maintaining biodiversity among *Escherichia coli*, and *Escherichia coli* varies continuously in order to avoid the sterilization from colicin; colicin has existed for billions of years, and it is still playing an irreplaceable physiological role in alimentary canal of each individual multicellular organism. Since the attacking target of novel antibiotics prepared by the method of this invention is microorganism or cell of other species, and these microorganisms or cells have never been attacked by colicin, it will cost much time for these bacteria to produce immune proteins similar with bacteria; accordingly, it is forecasted that novel antibiotics obtained by the method of this invention will have longer application lifetime than traditional antibiotics. By means of forming ion channel through target's membrane, colicin has strong sterilization effect, which is appropriately hundreds of even tens of thousands of times as that of traditional antibiotics, like penicillin, cynnematin, vancomycin, streptomycin, carbapenem, tigecycline, etc. Effect region selected preferably by the method of this invention will give much stronger sterilization effect to novel antibiotics prepared by the method of this invention, compared with traditional antibiotics.

In the case that both recognition region and effect region are recombinants of polypeptide molecule, the method of binding recognition region to effect region is preferably to synthesize the nucleotide sequence coding said recombinant, then to build recombinant expression vector loading said nucleotide sequence, finally to transform said recombinant expression vector into biological expression system, e.g., said recombinant is expressed in engineered strain of *Escherichia coli* and separated. Furthermore, engineered strain of *Escherichia coli* pET system, i.e., *E. coli* B834 (DE3) is selected preferably as biological expression system in the method of this invention, and the expression rate of said recombinant protein in this system is higher through verification.

About novel antibiotics prepared by the method of this invention, a batch of recombinants are gained in steps of obtaining recombinant, and the recombinants having recognition and pharmacological effects at least against targets, i.e., novel antibiotics are finally selected through conventional function verification, i.e., verification of recognition and pharmacological effects of recombinants by using their targets and non-targets. For some recombinants without effect on targets but with effects on non-targets, it is available to confirm their effect spectrum by further verification.

This invention also provides platform system of operating the above-mentioned method to develop novel antibiotics, which makes operation of the method to develop novel antibiotics standardized and modeled to enhance the efficiency of developing novel antibiotic. Said platform comprises 3 coordinated system groups: (1) goal proposing system, (2) designing system and (3) laboratory system.

Said goal proposing system determines development goal and give task instruction to designing system; the task of said goal proposing system is confirming which targets should be aimed at for developing novel antibiotics, what pharmacological effects the novel antibiotics carry out against said targets; for example, through search, demands of medicine field, drug-resistance status of antibiotics are analyzed, and new pathogens as well as information thereof and experimental data or outsourced contracting projects are collected as well as counted to confirm development goal. In this invention, said pharmaceutical effects are effects of regulating, repairing, marking, causing death and/or collapsing. Said goal proposing system may include core members of R&D team, marketing team; the fixed goal may be outsourced contracting projects, which designates to develop novel antibiotics against some pathogenic microorganisms.

Designing system designs recognition region, effect region and molecular structure of said recombinants and proposes the desired experimental task to laboratory system according to task instruction from goal proposing system and said general formula; it is required for designing system of novel antibiotics to establish recognition region library and effect region library in accordance with task instructions from goal proposing system. Based on instructions from goal proposing system, substances specifically recognizing said targets are collected, selected and prepared as recognition region; said preparing substances specifically recognizing said targets refers to preparing and screening to obtain monoclonal antibody specifically recognizing said targets through immunizing animals by using unique substances separated from said targets or said targets as immunogen;

said laboratory system offers experimental results to novel antibiotic designing system, and novel antibiotic designing system reports candidate products of finally-selected development achievements to goal proposing system;

said designing refers to the procedure of structural adjustment, structural recombination and/or structural confirmation based on molecular structure of the collected, selected or prepared substance.

In platform system of this invention, said laboratory system completes experimental work according to instruction from novel antibiotic designing system, for example, preparing monoclonal antibody of candidates as recognition region, preparing polypeptide as effect region and preparing said recombinants as well as carrying out a series of verification work. Basically, the work of said laboratory system includes preparing monoclonal antibody against target, obtaining amino acid sequence of monoclonal antibody by sequencing, synthesizing the gene of the designed antibody mimetic, synthesizing the gene coding recombinant, preparing as well as purifying recombinant or preparing recombinant, verifying recombinant, generating experimental report and giving feedback to designing system.

In development platform of this invention, designing system is the core of technology, and all works in laboratory system can be completed by prior art, thus, it is available to build a own completed laboratory work team, and it is also available to only arrange administrator for laboratory work team, and outsource laboratory work by laboratory system administrator to the $3^{rd}$ partner institutes who focus on experiment works of the corresponding stages. Through the above-mentioned process, development work can be completed with high-quality efficiently; research and development resources are integrated cost-effectively. Development platform established by this invention equals to an R & D factory of novel antibiotics.

Each system of said platform system of this invention performs its own function, coordinates to make the whole platform system work efficiently, which makes available that it only costs around half a year to generate a target novel antibiotic. In fact, a batch of novel antibiotics against one target was produced during this half a year, and antibiotic preparation efficiency is far higher than traditional preparation. In addition, the work of each system is carried out pointedly, accordingly fund of corporation or research institution is assigned with definite object, rather than invested blindly in projects without practically applicable significance or market demand. In particular, in platform of this invention, some works of system can be outsourced to a 3rd partner specialized in corresponding field. Consequently, not only can the high-efficient integration and utilization of R&D equipment and resources be realized, but also the R&D cost is lowered and the consumed time is shortened.

Workflow chart of said platform system of this invention is shown as FIG. 5, and it avoids wasting and repeating in development work at a maximum extent.

In summary, the method and platform system of this invention provide a new method for preparing medicine, and the advantages superior to traditional antibiotic preparation methods are as follows:

(1) non-subjecting to limitation of traditional method for screening antibiotics: novel antibiotics prepared by the method of this invention have common structural constitution, i.e., consist of effect region and recognition region. In development projects against targets with phospholipid bilayer cell membranes, it is available to select the current colicin as effect region; under introduction of recognition region, colicin of novel antibiotics can form lethal ion channel through almost all cell membranes with phospholipid bilayer cell membrane structure.

As there exists genus-unique or species-unique or strain-unique surface substances on surfaces of cell membranes in most microorganisms, preparing monoclonal antibody specifically recognizing the target by using said surface substances or cells containing said surface substances as immunogen is a very mature technology at present, and after obtaining said monoclonal antibody, antibody mimetic will be obtained as recognition region in light of the idea of designing antibody mimetic in previous inventions by inventor. Thereby, the development method of this invention will not be subjected to limitation that proteins as targets of drug effect (i.e., drug targets) discovered at present have been exhausted gradually, and the left targets are pharmacological significance (undruggable, i.e., do not react with drugs), and it is capable to develop novel antibiotics specifically against most pathogenic microorganisms.

(2) capacity of sensitively countering drug-resistance of pathogenic microorganism: because there is not only one surface antigen substance in pathogenic microorganism, it is available to select various surface substances on the surface of target microorganism for immunizing animal to generate corresponding monoclonal antibody, accordingly many kinds of antibody mimetic and mutamer thereof which can recognize said microorganism cell specifically are gained. As shown in FIG. 3, it is available to firstly select any of these antibody mimetics as the first recognition region of novel antibiotic developed by the method of this invention. After being used practically for a period of time, if said microorganism has occurred drug-resistance against said recognition region (e.g., structure of the corresponding surface substance (antigen) is modified to keep said recognition region from being recognized), it is available to select another from these antibody mimetics as the second recognition region, the third recognition region, the fourth recognition region of novel antibiotic developed by the method of this invention, accordingly to offer various optional novel antibiotics, which effectively overcomes the difficulty of failing to immediately provide alternative drug for treatment after drug-resistance occurring against antibiotics in prior art. The method of this invention is capable to extend the effective application lifetime of one novel antibiotic.

(3) the recognition region substances provided in said platform or method of this invention comprise, preferably comprise antibody mimetic, and mutamer by point mutation on short peptide of said antibody mimetic. Therefore, when mutation occurs on surface antigen of target pathogenic microorganism, there has existed not only one candidate antibody mimetic waiting for recognizing with said surface antigen, which makes the capacity of development method of this invention to counter drug-resistance further improved, as shown in FIG. 4.

(4) it is difficult for target to occur drug-resistance. In the method of this invention, it is preferable to select colicins as substances of effect region of novel antibiotics; bactericidal mechanism of colicin is different from that of most current antibiotics, and is not known well by pathogenic microorganisms; it will cost much time to occur drug-resistance in pathogenic microorganisms, which provides plenty of time to develop the next-generation antibiotics.

(5) By means of forming ion channel through target's membrane, colicin has strong sterilization effect, which is appropriately hundreds of even tens of thousands of times as that of traditional antibiotics, like penicillin, cynnematin, vancomycin, streptomycin, carbapenem, tigecycline, etc. As a preferred effect region of the method of this invention, it will give much stronger sterilization effect to novel antibiotics prepared by the method of this invention, compared with traditional antibiotics.

(6) Different from traditional method of screening antibiotics with long-time consuming, it is only required to cost 4-6 months to produce a batch of novel antibiotics against various pathogenic microorganisms through the method of this invention. The procedure is that, animal (mouse) is immunized using different antigens; the corresponding monoclonal antibody will be screened by haemospasia after 2 to 3 weeks of antibody production period; the nucleotide sequences coding variable region and backbone of heavy chain and light chain on Fab segment of monoclonal antibody are obtained by using protein sequencing and gene translation technology; according to the obtained nucleotide sequences, gene coding recognition region—antibody mimetic is designed, and it is bound to effect region—gene coding colicin to construct the recombinant plasmid; the engineered bacteria are transfected by said recombinant plasmid to express a novel antibiotic by proliferation. Afterwards, specificity and sensitivity of antibiosis and cytocidal effect of the separated and purified novel antibiotic are verified. It is only required about half a year to screen a batch of novel antibiotics by the whole procedure. Such high efficiency of construction and production will bring the revolutionary changes to traditional construction and production of antibiotics.

(7) The platform of this invention provides teamwork approach and resource utilization method to efficiently develop novel antibiotics. Since the developed antibiotics have common structural characteristics, through said platform of this invention, research and development resources are integrated effectively, and development work can be performed as flow-line production, which equals to a R & D factory of novel antibiotics.

In summary, method and platform system to develop novel antibiotics of this invention can offer novel antibiotics with specific recognition region and effect region against most pathogenic microorganisms and targets. For most targets, the currently-known bacteriocins are competent as the role of effect region, so development cycle of a novel antibiotic depends on the time to design molecular structure and the time to prepare as well as verify recombinants. Because recognition region depends not only on the selected nature substances but mainly depends on artificial-prepared antibody mimetic as recognition region, while obtaining monoclonal antibody through immunizing animals by using an immunogen and then getting amino acid sequence of said monoclonal antibody is a current mature technology, based on the current biotechnological level, the time to develop a novel antibiotic can be controlled in a short period basically. Platform for operating said development method of this invention fully optimizes, utilizes and integrates human resources and technology resources, to ensure efficient conduct of development process and make novel antibiotic development operating as flow-line production.

BRIEF DESCRIPTION OF THE DRAWINGS

FIG. 4 shows strategy 2 to construct recognition region.

FIG. 5 shows platform work flow chart, wherein M represents goal proposing system; D represents designing system; L represents laboratory system; double-headed arrow represents information exchange ways during preparation of novel antibiotics.

FIG. 6 shows comparison of in vitro killing effect of novel antibiotics against EB virus-induced Burkitt's lymphoma. (A) Control group, (B) group treated by novel antibiotics group 1.

FIG. 7 shows comparison of survival curves about inhibition of novel antibiotics prepared by this invention, wild-type colicin and anti-*Staphylococcus aureus* polypeptide (ZL 01128836.1) on methicillin-resistant *Staphylococcus aureus* (ATCC BAA-42), vancomycin-resistant enterococci (ATCC 700802), multi-drug resistant *Pseudomonas aeruginosa* (clinical isolated strain 13578 in West China Hospital); ordinate represents the minimum inhibitory concentration (nMol); wherein A is vancomycin-resistant enterococci, (1) anti-*Staphylococcus aureus* polypeptide, MIC=0.91 nMol, (2) wild-type colicin Ia, MIC=0.91 nMol, (3) PMC-AM1, MIC=0.23 nMol; B is methicillin-resistant *Staphylococcus aureus*, (1) anti-*Staphylococcus aureus* polypeptide, MIC=0.06 nMol, (2) wild-type colicin Ia, MIC=0.23 nMol, (3) PMC-AM1, MIC=0.06 nMol; C is multi-drug resistant *Pseudomonas aeruginosa*, (1) anti-*Staphylococcus aureus* polypeptide, MIC=0.91 nMol, (2) wild-type colicin Ia, MIC=0.91 nMol, (3) PMC-AM1, MIC=0.23 nMol.

FIG. 8A shows test results of inhibition of anti-cyanobacteria polypeptide against *Microcystis aeruginosa* growing in liquid medium; the left flask is control, and the right flask is anti-cyanobacteria polypeptide of 35 μg/ml.

FIG. 8B shows test results of inhibition of anti-cyanobacteria polypeptide against anabaena growing in liquid medium; the left flask is control, and the right flask is anti-cyanobacteria polypeptide of 35 μg/ml.

FIG. 8C shows test results of inhibition of anti-cyanobacteria polypeptide against chlorella growing in liquid medium; the left flask is control, and the right flask is anti-cyanobacteria polypeptide of 35 μg/ml.

FIG. 8D shows test results of inhibition of anti-cyanobacteria polypeptide against scenedesmus growing in liquid medium; the left flask is control, and the right flask is anti-cyanobacteria polypeptide of 35 μg/ml.

MODES OF CARRYING OUT THE INVENTION

Figure 1:
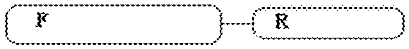
FIG. 1 shows general formula of novel antibiotic developed by the method of this invention: wherein F is effect region; R is recognition region.
Figure 2:
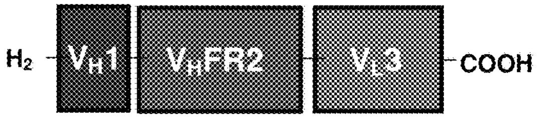
FIG. 2 shows structure of antibody mimetic.
Figure 3:
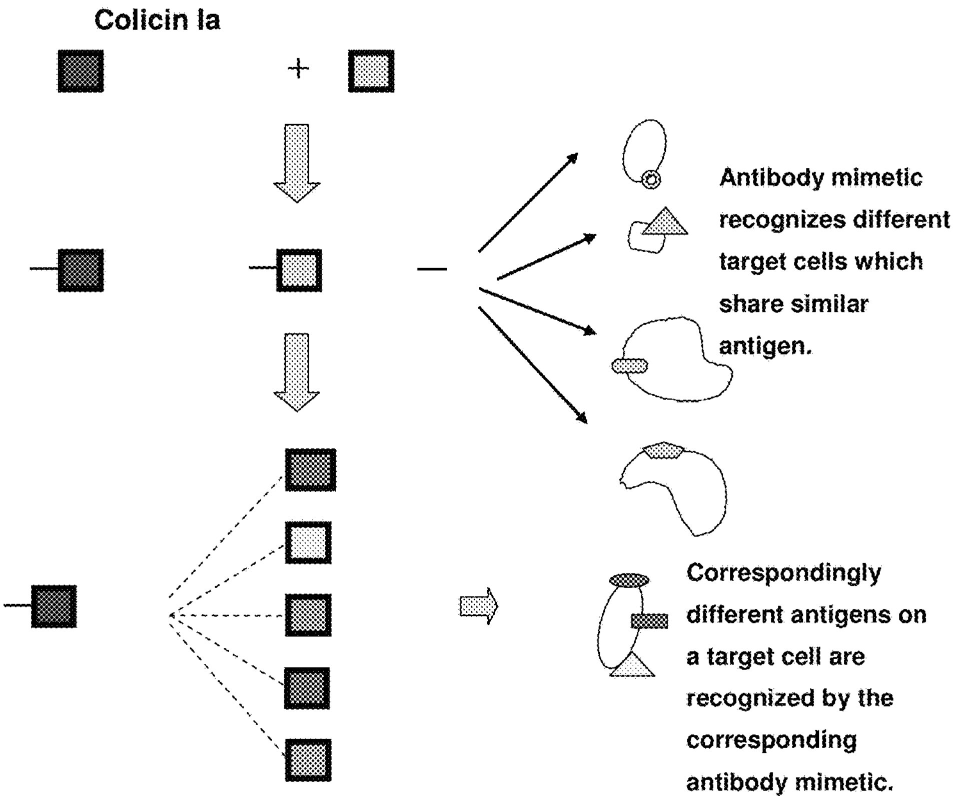
FIG. 3 shows strategy 1 to construct recognition region.

The method and platform of this invention will be described by the following currently-completed development examples.

Example 1 Preparation of Novel Antibiotics Against Virus-Induced Tumor (1) determining targets: to determine lethal novel antibiotics against EB virus-induced tumor cells.

(2) designing molecular structure of novel antibiotics: the following designing work was performed according to general formula

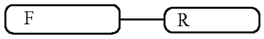

, wherein F is effect region; R is recognition region.

Establishing recognition region molecular structure library: monoclonal antibodies specifically-recognizing EB virus—anti-EB virus envelope glycoprotein antibodies gp320, i.e., monoclonal antibodies secreted by ATCC HB-168 hybridoma cells and amino acid sequences information thereof which had existed in prior art were found by searching in database.

Based on said monoclonal antibody, inventors designed a series of antibody mimetic structures as shown in Table 1, and obtained a series of mutamers through random point mutation on the first 5 and the last 9 amino acids of antibody mimetics with structures listed in Table 1.

TABLE 1

| The designed antibody mimetic structures |
|---|
| $V_H$CDR1-$V_H$FR2-$V_H$CDR3 |
| $V_L$CDR1-$V_H$FR2-$V_L$CDR3 |
| $V_H$CDR1-$V_H$FR2-$V_L$CDR3 |
| $V_H$CDR2-$V_H$FR2-$V_L$CDR3 |
| $V_L$CDR1-$V_H$FR2-$V_H$CDR3 |
| $V_L$CDR2-$V_H$FR2-$V_H$CDR3 |

Establishing effect region molecular structure library: because the preparation goal was lethal novel antibiotics against EB-virus induced tumor cells, colicin could form lethal ion channel through cell membrane of *Escherichia coli* of the same species but different strains by itself to cause death of *Escherichia coli* of the same species but different strains, and it was a competent candidate substance for effect region. Thus, colicins Ia, Ib, A, B and N or mutant sequence were selected as substances of effect region library and offered to laboratory system.

Preliminarily obtaining the designed molecular structure library of recombinants: from amino terminal to carboxyl terminal: colicin or mutamers thereof +28 peptides mimetic recognizing EB virus envelop glycoprotein, and molecular structures of some recombinants are shown in Table 2:

TABLE 2

| No. | Recognition region molecule | effect region molecule | Recombinant molecule (amino terminal-carboxyl terminal) |
|---|---|---|---|
| 1 | $V_H$CDR1-$V_H$FR2-$V_H$CDR3 | Ia | Ia-$V_H$CDR1-$V_H$FR2-$V_H$CDR3 |
| 2 | $V_L$CDR1-$V_H$FR2-$V_L$CDR3 | Ia | Ia-$V_L$CDR1-$V_H$FR2-$V_L$CDR3 |
| 3 | $V_H$CDR1-$V_H$FR2-$V_L$CDR3 | Ia | Ia-$V_H$CDR1-$V_H$FR2-$V_L$CDR3 |
| 4 | $V_H$CDR2-$V_H$FR2-$V_L$CDR3 | Ia | Ia-$V_H$CDR2-$V_H$FR2-$V_L$CDR3 |
| 5 | $V_L$CDR1-$V_H$FR2-$V_H$CDR3 | Ia | Ia-$V_L$CDR1-$V_H$FR2-$V_H$CDR3 |
| 6 | $V_L$CDR2-$V_H$FR2-$V_H$CDR3 | Ia | Ia-$V_L$CDR2-$V_H$FR2-$V_H$CDR3 |
| 7 | $V_H$CDR1-$V_H$FR2-$V_H$CDR3 | mIa (SEQ ID NO: 1) | mIa-$V_H$CDR1-$V_H$FR2-$V_H$CDR3 |
| 8 | $V_L$CDR1-$V_H$FR2-$V_L$CDR3 | mIa | mIa-$V_L$CDR1-$V_H$FR2-$V_L$CDR3 |
| 9 | $V_H$CDR1-$V_H$FR2-$V_L$CDR3 | mIa | mIa-$V_H$CDR1-$V_H$FR2-$V_L$CDR3 |
| 10 | $V_H$CDR2-$V_H$FR2-$V_L$CDR3 | mIa | mIa-$V_H$CDR2-$V_H$FR2-$V_L$CDR3 |
| 11 | $V_L$CDR1-$V_H$FR2-$V_H$CDR3 | mIa | mIa-$V_L$CDR1-$V_H$FR2-$V_H$CDR3 |
| 12 | $V_L$CDR2-$V_H$FR2-$V_H$CDR3 | mIa | mIa-$V_L$CDR2-$V_H$FR2-$V_H$CDR3 |

Note* monoclonal antibodies secreted by ATCC HB-168 hybridoma cells, $V_L$CDR1, $V_L$CDR2, $V_H$CDR1, $V_H$CDR2 $V_H$FR2, $V_L$CDR3, $V_H$CDR3, colicin Ia and amino acid sequence thereof as well as nucleotide sequence thereof are known, accordingly amino acid sequence and nucleotide sequence of recombinants can be deduced, and they will take too much space. Thereby, such sequence information will not be listed in this description.

(3) Laboratory system: recombinant library was obtained by binding the provided effect region and recognition region; gene coding said recombinant was inserted into expression vector to obtain recombinant expression vector; a batch of recombinant polypeptides were obtained by transforming said recombinant expression vector into engineered bacteria.

Anti-target verification experiment was conducted on the obtained recombinants (verification method and experimental design were the same as recorded in ZL2004/10081446.8). Recombinant 3 and 9 in Table 2 had the best killing effect against EB-virus induced tumor cells, and their results of in vitro killing experiment on EB-virus induced Burkitt's lymphoma are shown in FIG. 6; other 9 kinds of recombinants had different killing effects against EB virus-induced tumor, which are weaker than recombinant 3 and 9; all recombinants had no toxic and side effects on normal cells. The experimental process of verification is the same as recorded in Examples 2-5 of ZL2004/10081446.8.

Recombinants prepared by taking the mutants of antibody mimetics in recombinants 3 and 9 as recognition region were verified that, in Table 3, recombinants with SEQ ID NO: 2-6 as recognition region has basically equivalent killing effects against EB virus induced tumor cells as that of recombinant 3 or 9.

TABLE 3 amino acid sequences of 28 anti-EB virus induced tumor peptide mimetic $V_H$CDR1-$V_H$FR2-$V_L$CDR3 and mutamers thereof

| NO. | $V_H$CDR1-$V_H$FR2-$V_L$CDR3 and point mutants thereof |
|---|---|
| SEQ ID NO: 2 | SFGMHWVRQAPEKGLEWVAGQGYSYPYT |
| SEQ ID NO: 3 | SYGMHWVRQAPEKGLEWVAGQGYSYPYT |
| SEQ ID NO: 4 | SFGMHWVRQAPEKGLEWVAQQWSSNPYT |
| SEQ ID NO: 5 | SFGMHWVRQAPEKGLEWVALQGTHQPYT |
| SEQ ID NO: 6 | SFGMHWVRQAPEKGLEWVAQQLHFYPHT |
| SEQ ID NO: 7 | RQGMHWVRQAPEKGLEWVAGQGYSYPYT |

It took less than 6 months for this preparation, and a batch of candidate novel antibiotics with specific killing effect against targets were obtained successfully.

Experimental methods and materials adopted to obtain each recombinant in this example were exactly the same as recorded in Patent No. ZL2004/10081446.8, except for the inserted gene sequences when constructing vectors, so they are not repeated here.

Example 2 Preparation of Novel Antibiotics Against *Diplococcus intracellularis*

(1) determining targets: *diplococcus intracellularis.*

(2) designing molecular structure of novel antibiotics: the following designing work was performed according to general formula

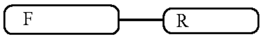

, wherein F is effect region; R is recognition region.

Establishing recognition region molecular structure library:

porin is one outer membrane protein which is common in gram-positive bacteria, like staphylococcus, streptococcus, enterococcus, gram-negative bacteria, like *Escherichia coli, Klebsiella pneumoniae, Pseudomonas aeruginosa, Acinetobacter baumannii, Enterobacter cloacae, Bacillus breslaviensis, Serratia marcescens, Aeromonas, Vibrio, Myxococcus*, and *Mycobacterium tuberculosis*; it is an ideal antigen protein, and PorA is one kind of porin.

Monoclonal antibody specifically-recognizing porin PorA which had existed in prior art was found by searching in database; PUBMED ID of its heavy chain peptide is 2 MPA_H, and PUBMED ID of its light chain peptide is 2 MPA_L. Based on said monoclonal antibody, inventors designed a series of antibody mimetic molecular structures as shown in Table 1 of Example 1.

Establishing effect region molecular structure library: because the preparation goal was lethal novel antibiotics against *Diplococcus intracellularis*, colicin was a competent candidate substance for effect region. Thus, colicins Ia, Ib, A, B and N were selected as substances of effect region library, and colicins Ia, Ib, A, B and N, ion channel domain molecules thereof and mutant molecules thereof constitute effect region molecular structure library.

The preliminarily designed molecular structure of recombinant library was: from amino terminal to carboxyl terminal: colicin or ion channel domain thereof or mutamers thereof +anti-PorA antibody mimetic and molecular structures of some recombinants are shown in Table 4:

TABLE 4

| NO. | Recognition region molecule | effect region molecule | Recombinant molecule (amino terminal to carboxyl terminal) |
|---|---|---|---|
| 1 | $V_H$CDR1-$V_H$FR2-$V_H$CDR3 | Ia | Ia-$V_H$CDR1-$V_H$FR2-$V_H$CDR3 |
| 2 | $V_L$CDR1-$V_H$FR2-$V_L$CDR3 | Ia | Ia-$V_L$CDR1-$V_H$FR2-$V_L$CDR3 |
| 3 | $V_H$CDR1-$V_H$FR2-$V_L$CDR3 | Ia | Ia-$V_H$CDR1-$V_H$FR2-$V_L$CDR3 |
| 4 | $V_H$CDR2-$V_H$FR2-$V_L$CDR3 | Ia | Ia-$V_H$CDR2-$V_H$FR2-$V_L$CDR3 |
| 5 | $V_L$CDR1-$V_H$FR2-$V_H$CDR3 | Ia | Ia-$V_L$CDR1-$V_H$FR2-$V_H$CDR3 |
| 6 | $V_L$CDR2-$V_H$FR2-$V_H$CDR3 | Ia | Ia-$V_L$CDR2-$V_H$FR2-$V_H$CDR3 |

Note* monoclonal antibodies specifically-recognizing porin PorA, and PUBMED ID of its heavy chain peptide is 2MPA_H; PUBMED ID of its light chain peptide is 2MPA_L, which are all-known. Thus, $V_L$CDR1, $V_L$CDR2, $V_H$CDR1, $V_H$CDR2 $V_H$FR2, $V_L$CDR3, $V_H$CDR3 are known, accordingly amino acid sequence and nucleotide sequence of recombinant molecules can be deduced exactly. Thereby, such sequence information will not be listed in this description.

(3) Laboratory system: gene coding said recombinant was inserted into expression vector to obtain recombinant expression vector; a batch of recombinant polypeptides were obtained by transforming said recombinant expression vector into engineered bacteria.

Anti-target verification experiment of the obtained recombinants was carried out. Verification experiment was conducted on the killing effects of the obtained recombinants against multi-drug resistant *Pseudomonas aeruginosa*, vancomycin-resistant enterococci, methicillin-resistant *Staphylococcus aureus, Acinetobacter baumannii, Klebsiella pneumoniae* and *Mycobacterium tuberculosis* (verification method and experimental design were the same as recorded in ZL2009/10092128.4). Recombinant 3 in Table 4 had the best killing effect against said pathogenic bacteria; comparison of survival curves about inhibition of novel antibiotics prepared by this invention on methicillin-resistant *Staphylococcus aureus* (ATCC BAA-42), vancomycin-resistant enterococci (ATCC 700802), multi-drug resistant *Pseudomonas aeruginosa* (clinical isolated strain 13578 in West China Hospital) is shown in FIG. 7; other 5 kinds of recombinants had different killing effects against said drug-resistant bacteria, which are weaker than recombinant 3; all recombinants had no toxic and side effects on normal cells. The experimental process of verification is the same as recorded in Examples 2-6 of ZL2009/10092128.4.

Recombinants prepared by taking the mutants of antibody mimetics in recombinant 3 as recognition region and taking colicin Ia as effect region were verified that, in Table 5, recombinants with SEQ ID NOS: 9-13 as recognition region has basically equivalent killing effects against the above-mentioned pathogenic bacteria as that of recombinant 3.

TABLE 5 amino acid sequences of anti-diplococcus intracellularis antibody mimetic $V_H$CDR1-$V_H$FR2-$V_L$CDR3 and mutamers thereof

| No. | $V_H$CDR1-$V_H$FR2-$V_L$CDR3 and point mutants thereof |
|---|---|
| SEQ ID NO: 8 | SYWLHWIKQRPGQGLWIGSQSTHVPRT |
| SEQ ID NO: 9 | SYGMHWIKQRPGQGLWIGSQSTHVPRT |
| SEQ ID NO: 10 | SYWIEWIKQRPGQGLWIGSQSTHVPRT |
| SEQ ID NO: 11 | NYWMHWIKQRPGQGLWIGSQSTHVPRT |

TABLE 5-continued amino acid sequences of anti-diplococcus intracellularis antibody mimetic $V_H$CDR1-$V_H$FR2-$V_L$CDR3 and mutamers thereof

| No. | $V_H$CDR1-$V_H$FR2-$V_L$CDR3 and point mutants thereof |
|---|---|
| SEQ ID NO: 12 | SYWLHWIKQRPGQGLWIGMQNIGLPWT |
| SEQ ID NO: 13 | SYWLHWIKQRPGQGLWIGQQFTSSPYT |

It took less than 6 months for this preparation, and a batch of candidate novel antibiotics with broad-spectrum antibacterial effect were obtained successfully.

Experimental methods and materials adopted to obtain each recombinant in this example were exactly the same as recorded in Patent No. ZL2009/10092128.4, except for the inserted gene sequences when constructing vectors, so they are not repeated here.

Example 3 Preparation of Novel Antibiotics Against *Bacillus anthracis*

(1) Goal proposing system determined anthrax toxin or *bacillus anthracis* as targets; lethal infection diseases caused by anthrax toxin or *bacillus anthracis* have been posing a huge threat against human health; in terrorist attacks, anthrax toxin is also the most horrible pathogen or toxin as weapon.

The goal of this preparation is to provide a novel antibiotic to destroy the toxicity of *bacillus anthracis* or anthrax toxin, i.e., to inhibit or interfere anthrax toxin PA antigen from forming active PA heptamer.

(2) Designing Novel Antibiotics:

The following designing work was performed according to general formula

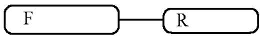

, wherein F is effect region; R is recognition region.

The general characteristic of anthrax toxin is that, anthrax toxin is a binary toxin with high harmfulness to organisms, and consists of protein antigen PA, necrosin and edema factor (LF/EF); protein antigen PA is a transport structure and can recognize target cells, and it transports necrosin and edema factor (LF/EF) into target cells. It is illustrated by animal experiments that, a combination of protein antigen and necrosin can immediately lead to cell death, while no reaction will be caused as applying said two components separately. The novel antibiotic was designed preliminarily that recognition region of said novel antibiotic can recognize anthrax PA antigen, and effect region of said novel antibiotic can inhibit or interfere anthrax toxin PA antigen from forming active PA heptamer.

Establishing recognition region molecular structure library: anti-*bacillus anthracis* protein antigen—lethal factor complex antibody (National Center for Biotechnology Information (NCBI) CAL58671) generated in cynomolgus and anti-*bacillus anthracis* protein antibody (NCBI ABF69350) generated in house mouse were found by searching database, and they are competent to specifically recognize protein antigen PA of anthrax toxin. According to amino acid information of said antibodies, a series of antibody mimetic structures and mutants thereof with a structure of $V_H$CDR1-$V_H$FR2-$V_L$CDR3 which can recognize wild-type anthrax toxin were designed to build recognition region molecular structure library, and provided to laboratory system.

Establishing effect region molecular structure library: because preparation goal is to inhibit anthrax toxin PA antigen from forming PA heptamer, in accordance with infection mechanism of anthrax toxin, in this experiment, some mutant anthrax toxin PA antigens (see SEQ ID NO:10 recorded in ZL2008/10045212.6) obtained by artificial mutation on anthrax toxin PA antigen were conducted as member of effect region molecular structure library, and PA lost recognition capacity to corresponding receptor on target cells; said mutant anthrax toxin PA antigen and wild-type anthrax toxin PA antigen constituted heterozygous PA heptamer, which lost transmembrane activity completely or partially, accordingly interfered with infection ability of anthrax toxin.

(3) Laboratory system: recombinant library was obtained by binding the provided effect region and recognition region; gene coding said recombinant was inserted into expression vector to obtain recombinant expression vector; a batch of recombinant polypeptides were obtained by transforming said recombinant expression vector into engineered bacteria.

A batch of recombinants with amino acid sequence listed in Table 6 as recognition region and mutant anthrax toxin PA antigens (see SEQ ID NO:10 recorded in ZL2008/10045212.6) as effect region were obtained through verification, and they could protect mice infected by *bacillus anthracis*. Verification experiment and results thereof were similar to the effects of pCHCA-PA1 recorded in ZL2008/10045212.6.

TABLE 6 amino acid sequences of antibody mimetics and mutamers thereof recognizing wild-type anthrax toxin PA

| NO. | $V_H$CDR1-$V_H$FR2-$V_L$CDR3 and its point mutants |
|---|---|
| SEQ ID NO: 14 | STALHWRQAPGKGLEWVPRYDEFPYT |
| SEQ ID NO: 15 | SFGMHWRQAPGKGLEWVPRYDEFPYT |
| SEQ ID NO: 16 | NYWMHWRQAPGKGLEWVPRYDEFPYT |
| SEQ ID NO: 17 | STALHWRQAPGKGLEWVFQGSHVPFT |
| SEQ ID NO: 18 | STALHWRQAPGKGLEWVYCHQWSMYT |
| SEQ ID NO: 19 | STALHWRQAPGKGLEWVQQWSSNPYT |
| SEQ ID NO: 20 | STALHWRQAPGKGLEWVQQFTSSPYT |

It took less than 6 months for this preparation, and a batch of novel antibiotics which have protection effects against *bacillus anthracis* infection were obtained successfully.

Experimental methods (e.g., vector construction, transformation, verification experiment, etc.) and materials adopted to obtain each recombinant in this example were exactly the same as examples recorded in Patent No. ZL2008/10045212.6, except for the inserted gene of novel antibiotics, so they are not repeated here.

Example 4 Preparation of Novel Antibiotics Against Fungi (1) Goal proposing system determined *Candida albicans* as targets, and the goal was determined to prepare novel antibiotics killing agricultural fungus—*Candida albicans.*

(2) Designing novel antibiotics:

The following designing work was performed according to general formula

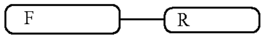

, wherein F is effect region; R is recognition region.

Establishing recognition region molecular structure library: the great progress in fungus basic research had been achieved in recent years; amino acid sequence (SEQ ID NO:21) of *Candida albicans* pheromone consists of 14 amino acid residues. It can move around freely in biological media, and has biological activity of automatically searching the corresponding receptor on cell membranes of the same species of fungi cells. Thus, based on such automatically searching activity, it is available to utilize fungus pheromone as recognition region to induce effect region like bacterial exotoxin such as colicin to kill these fungi by forming ion channel through cell membranes, and a batch of novel biological biocides were constructed accordingly.

Therefore, *Candida albicans* pheromone represented by SEQ ID NO:21 was selected as recognition region.

Establishing effect region molecular structure library: because the preparation goal was lethal novel antibiotics against target of agricultural fungus-*Candida albicans*, colicin was a competent candidate substance for effect region owing to its characteristics. Thus, colicins Ia, Ib, A, B and N, and ion channel domains thereof were selected as members of effect region molecular structure library, and were provided to laboratory system.

The preliminarily designed molecular structure of novel antibiotic was: from amino terminal to carboxyl terminal: colicin or ion channel domain thereof or mutamers thereof +*Candida albicans* pheromone.

(3) Laboratory system: recombinant library was obtained by binding the effect region and recognition region; gene coding said recombinant was inserted into expression vector to obtain recombinant expression vector; recombinant polypeptides were expressed by transforming said recombinant expression vector into engineered bacteria, which realized operable binding between effect region and recognition region.

The obtained recombinants were verified that, they all have protection effects on rice (*Oryza sativa*) infected by fungi like *Pyricularia oryzae, Aspergillus flavus*, and their protection effect on rice blast infection is thousands of times higher than that of current agricultural antifungal.

Experiments and data (e.g., vector construction, transformation) related to obtaining each recombinant in this preparation was recorded in examples of Patent No. ZL2007/10050926.1 or based on the record in prior art, person skilled in the art can obtain the experimental methods required for the preparation of this invention by a limited number of experiments, so they are not repeated here.

It took 6 months for this preparation, and cost only 1.5-2 years including field experiments, whose efficiency and success rate are far higher than that of current preparation for a new drug.

Example 5 Preparation of Novel Antibiotics Against Drug-Resistant *Staphylococcus aureus*

(1) goal proposing system determined *Staphylococcus aureus* as targets: since antibiotics like penicillin was applied in 1944, bacteria, especially pathogenic bacteria threatening human life, like *Staphylococcus aureus, streptococcus pneumonia, Pseudomonas aeruginosa, mycobacterium tuberculosis*, etc., have generated drug-resistance, and human are urgent to develop novel antibiotics against drug-resistant bacteria.

(2) Designing novel antibiotics:

The following designing work was performed according to general formula

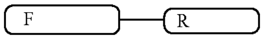

, wherein F is effect region; R is recognition region.

Establishing recognition region molecular structure library: many cells secrete signal transduction polypeptides to the outside of cells; these polypeptides can automatically search for the corresponding receptors on cell membranes of the same species of bacteria, and bind to said receptors to transport information into said bacteria; *staphylococcus* secretes signal transduction polypeptides to the outside of cells; these polypeptides can automatically search for the corresponding receptors on cell membranes of the same species of bacteria, and bind to said receptors to transport information into said bacteria. These signal transduction polypeptides consist of several to more than 10 amino acids, and are ideal recognition regions against *staphylococcus*. Pheromone sequences as SEQ ID NOS:22-26 were collected as the members of recognition region library through searching.

Providing effect region: because the preparation goal was lethal novel antibiotics against target of drug-resistant *Staphylococcus aureus-Candida albicans*, colicin was a competent candidate substance for effect region owing to its characteristics. Thus, colicins Ia, Ib, A, B and N, and ion channel domains thereof were selected as effect regions, and were provided to laboratory system.

The preliminarily designed molecular structure of novel antibiotic was: from amino terminal to carboxyl terminal: colicin or ion channel domain thereof or mutamers thereof +pheromone, and pheromone+colicin or ion channel domain thereof or mutamers thereof.

(3) Laboratory system: recombinant library was obtained by binding the effect region and recognition region; synthetic gene coding said recombinant was inserted into expression vector to obtain recombinant expression vector; recombinant polypeptides were expressed by transforming said recombinant expression vector into engineered bacteria, which realized operable binding between effect region and recognition region.

A batch of recombinants were obtained, such as recombinant polypeptide expressed by recombinant plasmids pBHC-SA1, pBHC-SA2, pBHC-SA3 pBHC-SA4, pBHC-SE and pBHC-PA (as recorded in Patent No. ZL2009/10157564.5). They all have significant killing effects against methicillin-resistant *Staphylococcus aureus*, penicillin-resistant *Staphylococcus aureus*, vancomycin-resistant enterococci, *Pseudomonas aeruginosa* and multi-drug resistant *Pseudomonas aeruginosa.*

Experiments and data (e.g., vector construction, transformation) related to obtaining each recombinant in this preparation was recorded in examples of Patent No. ZL2009/10157564.5 or based on the record in prior art, person skilled in the art can obtain the experimental methods required for the preparation of this invention by a limited number of experiments, so they are not repeated here.

It took 5 months to prepare a batch of novel antibiotics against drug-resistant bacteria, whose efficiency and success rate are far higher than that of current preparation for a new drug.

Example 6 Preparation of Novel Antibiotics Against Cyanobacteria (1) Goal proposing system determined cyanobacteria as targets: cyanobacteria proliferation caused by water eutrophication, water pollution are the severest harm threatening water environment in the world, and they result in huge economic loss to human as well as cause unrepaired harm to earth's biosphere. As the accelerated industrialization and urbanization caused by Chinese economic development, ecological environment pollution and degeneration aggravate gradually, and water environment ecological control has been major problem we must face and solve. The current antimicrobial drugs almost have little effects against cyanobacteria; cyanobacteria is prokaryotic cell belonging to cyanobacteria phylum of bacteria kingdom, and only chemicals of heavy metals can control cyanobacteria at present, e.g., cupric sulfate. However, in practical application, owing to limited effects, it is required to use chemical with overdose repeatedly, and other beneficial algae, aquatic plants and aquatic organisms are destroyed when killing cyanobacteria, which results in irreversible permanent damage to environment.

The purpose is preparing novel antibiotics killing or inhibiting cyanobacteria.

(2) Designing novel antibiotics:

The following designing work was performed according to general formula

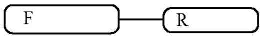

, wherein F is effect region; R is recognition region.

Establishing recognition region molecular structure library: a batch of hybridoma cells secreting anti-cyanobacteria monoclonal antibodies were obtained by immunizing mice with cyanobacteria as antigen, and the deposit No. of one strain of said hybridoma cells is CGMCC No. 4783.

Based on amino acid sequences of said monoclonal antibodies obtained by sequencing, a batch of antibody mimetics were designed, which are shown in Table 1, and mutamers of antibody mimetics were obtained through random point mutation on the first 5 and the last 9 amino acids of antibody mimetics; recognition region molecular structure library was built by taking said antibody mimetic molecules and mutamers thereof as members. Wherein, the amino acid sequence of antibody mimetic with a structure of $V_H$CDR1-$V_H$FR2-$V_L$CDR3 of monoclonal antibody secreted by hybridoma cells (CGMCC No. 4783) is shown as SEQ ID NO:27.

Establishing effect region molecular structure library: because the preparation goal was novel antibiotics killing or inhibiting cyanobacteria, colicin could form lethal ion channel through cell membrane of *Escherichia coli* of the same species but different strains by itself to cause death of *Escherichia coli* of the same species but different strains, and it was a competent candidate substance for effect region. Thus, colicins Ia, Ib, A, B and N or mutant sequences thereof were selected as members of effect region molecular structure library.

Preliminarily obtaining the designed molecular structure of novel antibiotics: from amino terminal to carboxyl terminal: colicin or mutamers thereof+anti-cyanobacteria antibody mimetic/mutamers:

(3) Laboratory system: molecular structure of recombinants was obtained by binding the effect region and recognition region; gene coding said recombinant was inserted into expression vector to obtain recombinant expression vector; the recombinants were expressed by transforming said recombinant expression vector into engineered bacteria and isolated.

It is revealed by verification on the inhibition effect of obtained recombinants against cyanobacteria (the design and operation of verification experiments was the same as recorded in Examples 3-5 of ZL2011/10155221.2) that, said recombinants had significant inhibition effects on *Microcystis aeruginosa*, anabaena but no inhibition on other beneficial algae like chlorella, diatom and scenedesmus. Some experimental results are shown as FIG. 8A-8D. The molecular structures of some selected recombinants are listed in Table 7.

TABLE 7 amino acid sequences of antibody mimetics and mutamers against surface antigens of *Microcystis aeruginosa*

| NO. | $V_H$CDR1-$V_H$FR2-$V_L$CDR3 and point mutants thereof |
|---|---|
| SEQ ID NO: 27 | SYWMQWVKQRPGQGLEWIGQQYWSTPPWT |
| SEQ ID NO: 28 | SYGMHWVKQRPGQGLEWIGQQYWSTPPWT |
| SEQ ID NO: 29 | DHYMHWVKQRPGQGLEWIGQQYWSTPPWT |
| SEQ ID NO: 30 | SYWIEWVKQRPGQGLEWIGQQYWSTPPWT |
| SEQ ID NO: 31 | SYWMQWVKQRPGQGLEWIGQQQFTSSPWT |
| SEQ ID NO: 32 | SYWMQWVKQRPGQGLEWIGQQQSREYPYT |
| SEQ ID NO: 33 | SYWMQWVKQRPGQGLEWIGQLQGTHQPYT |

It took less than 11 months for this preparation, and a batch of verified novel antibiotics which had killing effects against targets were obtained successfully.

Experimental methods and materials adopted to obtain recombinants in this preparation were exactly the same as recorded in Patent No. ZL2011/10155221.2, except for the inserted gene of novel antibiotics in vector construction, so they are not repeated here.

Example 7 Experiments of Screening Suitable Biological Expression Systems for the Methods of this Invention Recombinant plasmids were obtained during novel antibiotics preparation recorded in examples 5-6: pBHC-SA1, pBHC-SA2, pBHC-SA3, pBHC-SA4, pBHC-SE, pBHC-PA and pBHC-PorA1.

Step 1. Transforming Competent Cells

4040 μl various engineered bacteria of pET system like BL-21(DE3), B834(DE3), Nova Blue(DE3) and 618 (Novagen) were transfected by 100 ng recombinant mutant plasmids respectively; ice incubate for 5 minutes, thermal shock at 42° C. for 30 seconds, ice bathing for 2 minutes, adding 160 ul SOC medium, 220 rpm, incubated at 37° C. by shaking for 1 hour, and then spread on plate (LB medium with 1% agar and 50 μg/ml ampicillin) to incubate at 37° C. overnight. Monoclonal colony was selected for proliferation to get strain, and the strain was preserved at low temperature.

Step 2. Strain Recovery

1. Strain Recovery

Said preserved strain was unfrozen at 4° C.; 1.5 ml strain was added in 10 ml LB medium (containing AMP 50 μg/ml), 220 rpm, and incubated at 37° C. for 5-8 hours.

2. Inoculation of Monoclonal Strain

The recovered strain culturing liquid was diluted at $10^4$ or $10^5$ times; 10 μl diluted strain culturing liquid was placed onto the prepared LB solid medium (AMP 50 μg/ml) plate and spread. The plates were placed in moist box for incubation at 37° C. for 10-12 hours till round single colonies were raised on the surface of plate.

Step 3. Selection and Proliferation of Strain (1) Regular round single colony with smooth edge was selected by the sterilized toothpick or inoculation loop from the incubated plate, and placed into 1.5 ml LB medium for culture by shaking at 220 rpm and 37° C. for 5-8 hours.

(2) 1.5 ml LB medium was added into 100 ml LB medium for culture by shaking at 220 rpm and 37° C. for 5-8 hours.

(3) $1^{st}$ grade amplification culture: 100 ml strain culturing liquid obtained from the last step was added into 700 ml improved FB-M9 complex medium for culture by shaking at 220 rpm and 37° C. for 5-8 hours.

(4) $2^{nd}$ grade amplification culture: 700 ml strain culturing liquid obtained from the last step was added into 6×700 ml improved FB-M9 complex medium for culture by shaking at 220 rpm and 37° C. for 5-8 hours.

(5) 3rd grade amplification culture: 6×700 ml strain culturing liquid obtained from the last step was added into 20 L improved FB-M9 complex medium for culture in fermenter with shaking speed at 220 rpm and maximum oxygen content, at 37° C. for 3-5 hours.

(6) Engineered bacteria fermentation and induction of protein expression: 20 L strain culturing liquid obtained from the last step was added into 200 L improved FB-M9 complex medium for culture and protein expression in fermenter, with shaking speed at 220 rpm and maximum oxygen content, at 30° C. for 2-4 hours; then at 42° C. for 0.5 hours; finally at 37° C. for 1-2 hours. Note: IPTG with final concentration of 0.5 mM was added when reaching 42° C.

Step 4. Strain Collection by Centrifugation

Strain culturing liquid was centrifuged at 6000 g, 4° C. for 20 min. The precipitate was collected after centrifugation, and resuspended in 50 mM borate buffer (pH9.0). Note: 2 mM PMSF (benzyl sulfuryl fluoride serine proteases inhibitor) was added into borate buffer, and the operation after thalli resuspending must be conducted at 4° C.

Step 5. Thalli Fragmentation

After thalli were suspended in pH9.0 borate buffer totally, thalli were fragmentated by high pressure homogenizer at 500-600 bar; fragmentation was repeated for 7 times, and there was 3-5 minutes interval between two fragmentations.

Step 6. Precipitation of Thalli DNA

Fragmentated strain culturing liquid was centrifuged at 55000 g, 4° C. for 40 min. The supernatant was isolated, added with streptomycin sulfate (16 bottles of streptomycin sulfate with 1 million units were added into every 200 ml liquid), and stirred on magnetic stirrer for 1 h.

Step 7. Dialysis

Strain culturing liquid obtained by the last step was centrifuged at 55000 g, 4° C. for 20 min. The supernatant was isolated, placed into dialysis bag, placed in borate buffer for dialysis for 8-12 hours, and the dialysate was changed once every 4 hours.

Step 8. Antibacterial Engineered Polypeptide Medicine Obtained by Protein Purification Strain culturing liquid after dialysis was centrifuged at 55000 g, 4° C. for 20 min. The supernatant was placed into beaker to conduct protein purification by ion exchange method. The supernatant was loaded in CM ion exchange column, and protein concentration was detected to count protein content per unit volume; the ratio of loading volume and CM ion gel particles was fixed according to operation manual. After rinsing thoroughly, novel antibacterial engineered polypeptide was obtained through elution by 50 mM borate buffer containing 0.2M NaCl.

It is described by results shown in Table 8 that, the expression rate of PMC-SA in *E. coli* B834 (DE3) was the highest.

TABLE 8 comparison of expression rates in different strains

| Engineered strains | TG1 | BL-21 | 618 | NavaBlue | B834 |
|---|---|---|---|---|---|
| the average yield per unit (mg/L) | 0.8 | 10 | 5.8 | 8.1 | 24.4 |

(the average yield per unit = total production of extracted PMC-SA1/the volume of strain culturing liquid)

The same operation and comparison were conducted on other 6 kinds of recombinant mutant plasmids, and the results all show the same tendency as shown in Table, that is, compared with other engineered bacteria, the expression rates of 7 kinds of recombinant mutant plasmids in *E. coli* B834(DE3) are all the highest.

On the basis of this screening experiment, it is preferable but not limited to select *E. coli* B834(DE3) as expression system in the method of this invention, in order to efficiently express and prepare to obtain novel antibiotics.

In summary, novel antibiotic preparation method and platform system of this invention are capable of providing novel antibiotics with recognition region and effect region specifically against most pathogenic microorganisms and targets. For most targets, the currently-known colicin is competent to playing the role of effect region, so the cycle time of preparing a novel antibiotic depends on the time to design molecular structure, the time to provide recognition region molecular information, as well as the time to prepare and verify recombinants. Because recognition region depends not only on the selected nature substances but mainly depends on artificial-prepared antibody mimetic as recognition region, in view of the current biotechnological level, the time to prepare a novel antibiotic can be basically controlled in a very short period. Platform for operating said preparation method of this invention fully optimizes, utilizes and integrates human resources and technology resources, to ensure efficient conduct of development process and make novel antibiotic development operating as flow-line production.

The invention claimed is:

1. A method of identifying an agent that inhibits growth, proliferation, and/or survival of a virus or cell, wherein the agent comprises a recognition moiety and an effector moiety, the method comprising:

(a) providing a first library of polynucleotides each encoding an antibody mimetic having the structure $V_H$CDR1-$V_H$FR2-$V_L$CDR3 from N-terminal to C-terminal which is constituted by regions $V_H$CDR1, $V_H$FR2, and $V_L$CDR3 on Fab short arm of an immunoglobulin, wherein the amino acid sequence of the antibody mimetic has a sequence selected from the group consisting of SEQ ID NOs: 8-13, SEQ ID NOs: 14-20, SEQ ID NOs: 27-33, and a combination thereof, wherein (i) the antibody mimetic is a recognition moiety for a target molecule on the surface of a virus or cell, and (ii) regions of $V_H$CDR1, $V_H$FR2, and $V_L$CDR3 are from an antibody that specifically recognizes a target molecule on the surface of the virus or cell;

(b) providing a second library of polynucleotides each encoding an effector moiety that inhibits a property of the virus or cell, wherein (i) the effector moiety is selected from the group consisting of colicin Ia, colicin Ib, colicin A, colicin B, and colicin N, and (ii) the property of the virus or cell is selected from the group consisting of growth, proliferation, survival and a combination thereof;

(c) constructing a third library of recombinant polynucleotides, each recombinant polynucleotide of the third library of recombinant polynucleotides comprising a polynucleotide of the first library operably linked to a polynucleotide of the second library;

(d) expressing the third library of recombinant polynucleotides in a biological expression system to generate a fourth library of fusion polypeptides;

(e) screening the fourth library of fusion polypeptides to identify a fusion polypeptide that specifically recognizes the target molecule on the surface of the virus or cell and inhibits a property of the virus or cell, thereby identifying an agent comprising the identified fusion polypeptide as one that inhibits growth, proliferation, and/or survival of the virus or cell.

2. The method according to claim 1, wherein the second library comprises a polynucleotide comprising the sequence set forth in SEQ ID NO: 1.

3. The method according to claim 1, wherein the agent protects a mammal from an infection, a toxin, and/or death.

4. The method according to claim 3, wherein the infection is a *Bacillus anthracis* infection and the toxin is a necrosin or an edema factor.

5. The method according to claim 3, wherein the recognition moiety of the agent recognizes a wild-type *Bacillus anthracis* protective antigen (PA), and the effector moiety of the agent comprises a mutant *Bacillus anthracis* PA that forms a heterozygous PA heptamer with the wild-type *Bacillus anthracis* PA, and the heterozygous PA heptamer, in comparison to a wild-type PA heptamer, has no or a reduced ability to transport a *Bacillus anthracis* toxin across a cell membrane.

6. The method according to claim 1, wherein said antibody is generated by immunizing an animal with the cell or the target molecule or a portion thereof as an immunogen.

7. The method according to claim 1, wherein said antibody is generated by immunizing an animal with a plurality of target molecules or portions thereof as immunogens.

8. The method according to claim 1, wherein said antibody comprises a plurality of monoclonal antibodies, and the $V_H$CDR1 and $V_L$CDR3 are from the same monoclonal antibody or from different monoclonal antibodies.

9. The method according to claim 1, wherein the cell is a Gram-negative bacterium or a Gram-positive bacterium.

10. The method according to claim 1, wherein the biological expression system for the third library is an *Escherichia coli* (*E. Coli*) pET expression system.

11. The method according to claim 10, wherein the *E. coli* pET system is BL-21(DE3) or B834(DE3).

12. The method according to claim 1, further comprising separating and/or purifying the identified fusion polypeptide.

* * * * *